US009403877B2

(12) United States Patent
Agrez

(10) Patent No.: US 9,403,877 B2
(45) Date of Patent: Aug. 2, 2016

(54) PEPTIDE AGENTS FOR CANCER THERAPY

(71) Applicant: INTER-K PTY LIMITED, Newcastle, New South Wales (AU)

(72) Inventor: Michael Valentine Agrez, Charlston (AU)

( * ) Notice: Subject to any disclaimer, the term of this patent is extended or adjusted under 35 U.S.C. 154(b) by 0 days.

(21) Appl. No.: 14/374,245

(22) PCT Filed: Jan. 24, 2013

(86) PCT No.: PCT/AU2013/000045
§ 371 (c)(1),
(2) Date: Jul. 24, 2014

(87) PCT Pub. No.: WO2013/110120
PCT Pub. Date: Aug. 1, 2013

(65) Prior Publication Data
US 2015/0110744 A1    Apr. 23, 2015

(30) Foreign Application Priority Data

Jan. 24, 2012 (AU) ................................ 2012900259
Oct. 6, 2012 (AU) ................................ 2012904368

(51) Int. Cl.
| C07K 14/01 | (2006.01) |
| C07K 14/00 | (2006.01) |
| C07K 14/705 | (2006.01) |
| A61K 38/00 | (2006.01) |
| C07K 7/06 | (2006.01) |
| C07K 7/08 | (2006.01) |
| A61K 38/08 | (2006.01) |
| A61K 38/10 | (2006.01) |
| A61K 38/16 | (2006.01) |

(52) U.S. Cl.
CPC ............. *C07K 14/001* (2013.01); *A61K 38/005* (2013.01); *A61K 38/08* (2013.01); *A61K 38/10* (2013.01); *A61K 38/16* (2013.01); *C07K 7/06* (2013.01); *C07K 7/08* (2013.01); *C07K 14/70546* (2013.01); *C07K 2319/10* (2013.01)

(58) Field of Classification Search
CPC ...................................................... C07K 14/01
See application file for complete search history.

(56) References Cited

U.S. PATENT DOCUMENTS

| 6,696,546 B1 | 2/2004 | Bond |
| 7,183,105 B2 | 2/2007 | Sabbadini |
| 7,611,885 B2 | 11/2009 | Brahmbhatt |
| 8,003,091 B2 | 8/2011 | Brahmbhatt |
| 2003/0040089 A1 | 2/2003 | Legrain |
| 2006/0063731 A1 | 3/2006 | Lewis |
| 2006/0063924 A1 | 3/2006 | Ni |

FOREIGN PATENT DOCUMENTS

| WO | WO 01/00677 | * | 1/2001 | ............ C07K 14/71 |
| WO | WO-0100677 | | 1/2001 | |
| WO | WO-0193836 | | 12/2001 | |
| WO | WO-02051993 | | 7/2002 | |
| WO | WO-03033519 | | 4/2003 | |
| WO | WO-03044172 | | 5/2003 | |
| WO | WO 2005/037308 | * | 4/2005 | ............ A61K 38/45 |
| WO | WO-2005037308 | | 4/2005 | |
| WO | WO-2005105837 | | 11/2005 | |
| WO | WO-2006029005 | | 3/2006 | |
| WO | WO-2006029981 | | 3/2006 | |
| WO | WO-2006031689 | | 3/2006 | |
| WO | WO-2006031996 | | 3/2006 | |
| WO | WO-2007039728 | | 4/2007 | |
| WO | WO-2009013127 | | 1/2009 | |
| WO | WO-2009106073 | | 9/2009 | |
| WO | WO-2010039778 | | 4/2010 | |
| WO | WO-2010094085 | | 8/2010 | |

OTHER PUBLICATIONS

Agrez MV, et al., Multiplicity of fibronectin-binding αv integrin receptors in colorectal cancer. British Journal of Cancer (1996) 73, 887-892.
International Search Report for PCT/AU2010/000203, mailed on Apr. 22, 2013.
Written Opinion of the International Preliminary Examining Authority for PCT/AU2010/000203, mailed on Dec. 9, 2013.
Ahmed N, et al. (2002) Direct integrin αvβ6-ERK binding: implications for tumour growth. Oncogene 21: 1370-1380.
Ahmed N, et al. (2002), Overexpression of αvβ6 integrin in serous epithelial ovarian cancer regulates extracellular matrix degradation via the plasminiogen activation cascade. Carcinogenesis 23:237-244.
Agrez M.V., The αvβ6 integrin induces gelatinase B secretion in colon cancer cells. Int. J. Cancer 81, 90-97 (1999).
Agrez et al., Synergistic anti-tumour effect of cisplatin when combined with an anti-Src kinase integrin based peptide. J Cancer Therapy, 2(3); Aug. 2011: doi:10.4236/jct.2011.23039.
Cheng JQ et al. (1996) Amplification of AKT2 in human pancreatic cancer cells and inhibition of AKT2 expression and tumorigenicity by antisense RNA. PNAS 93: 3636-3641.

(Continued)

*Primary Examiner* — Amber D Steele
(74) *Attorney, Agent, or Firm* — Flener IP Law, LLC; Zareefa B. Flener

(57) ABSTRACT

There is provided peptides for inhibiting growth of cancer cells, the peptides comprising the amino acid sequence RxKxKxxxxR wherein K and R are respectively lysine and arginine amino acid residues, each x is independently an amino acid, and 5 wherein the peptide has 50% or less amino acid sequence identity with the amino acid sequence RSKAKNPLYR (SEQ ID. No. 2). Each x amino acid may independently be an amino acid residue selected from the group consisting of alanine (A), valine (V), leucine (L), isoleucine (I), threonine (T) and serine (S) amino acid residues. There is also provided chimeric proteins incorporating a peptide of the amino acid sequence 10 RxKxKxxxxR, nucleic acids encoding for the peptide, expression vectors including a nucleic acid encoding the peptide for expression of the peptide, and methods for use of the peptide for inhibiting growth of cancer cells.

21 Claims, 6 Drawing Sheets

(56) References Cited

OTHER PUBLICATIONS

Figure 1:
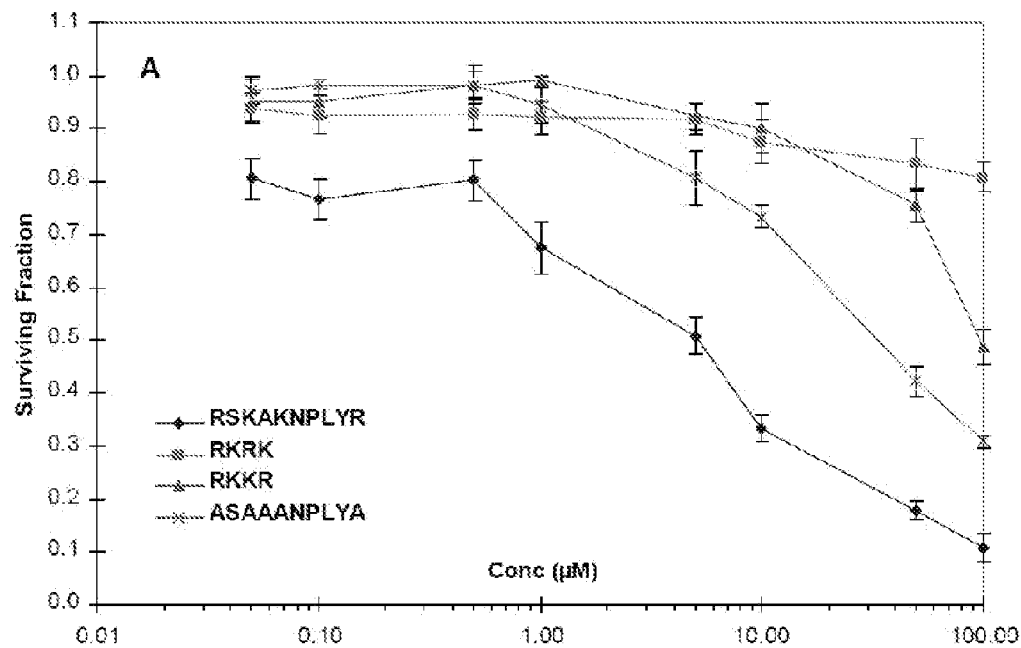

Cheng JQ et al. (2005) The AKT/PKB pathway: molecular target for cancer drug discovery. Oncogene 24: 7482-7492.

De Boer PA, et al., A division inhibitor and topological specific factor coded for by the miicell locus determine proper placement of the division septum in *E.coli*. Cell, 56; 641-649, 1989.

Filadro EJ et al(1995) Requirement of the NPXY motif in the integrin beta 3 subunit cytoplasmic tail for melanoma cell migration in vitro and in vivo. J Cell Biol 130: 441-450.

Huang D. et al., Bcl-2, Bcl-xL and adenovirus protein E1B19kD are functionally equivalent in their ability to inhibit cell death, Oncogene (1997) 14:405-414.

Kim H.H. et al. (2005) Basic peptide system for efficient delivery of foreign genes. Biochimica et Biophysica Acta (BBA), 2003; 1640: 129-136.

Lee C.C. et al., Designing dendrimers for biological applications. Nature Biotech. 23, 1517-1526 (2005).

MacDiarmid JA., Bacterially Derived 400 nm Particles for Encapsulation and Cancer Cell Targeting of Chemotherapeutics (2007), Cancer Cell; 11;431-445.

Sadler K. and Tam J.P. Peptide dendrimers: applications and synthesis. Rev. Mol. Biotechnology. 90, 195-229, (2002).

Takada Y et al. Protein family review—The integrins. Genome Biology, 2007; 8 (5): 215.

Agrez MV et al., The αvβ6 Integrin Promotes Proliferation of Colon Carcinoma Cells through a Unique Region of the β6 Cytoplasmic Domain The Journal of Cell Biology vol. 127, 2: 547-556 (1994).

Hassell TC et al., Synthetic peptides derived from the nonmuscle myosin light chains are highly specific substrates for protein Kinase C. Biochimica et Biophysica Acta., 1988, vol. 957, pp. 1-10.

McLeod, MP et al., The complete genome of *Rhodoccus* sp. RHAI provides insights into a catabolic powerhouse. PNAS., 2006, vol. 103, No. 42, pp. 15582-15587 & Chemical Abstracts Accession No. 2006: 1145229.

Riken Genome Exploration Research Group and Genome Science Group (Genome Network Project Core Group) and the Fantom Consortium. Antisense Transcription in the Mammalian Transcriptome. Science, 2005, vol. 309, pp. 1564-1566 & Chemical Abstracts Accession No. 2005: 1205849.

Xu, B.X., et al., The N-terminal ERK-binding Site of MEK1 Is Required for Efficient Feedback Phosphorylation by ERK2 in Vitro and ERK Activation in Vivo. The Journal of Biological Chemistry, 1999. vol. 274, No. 48, Issue of Nov. 26, pp. 34029-34035.

* cited by examiner

PEPTIDE AGENTS FOR CANCER THERAPY

FIELD OF THE INVENTION

The invention relates to agents for the inhibition of the growth and/or proliferation of cancer cells.

BACKGROUND OF THE INVENTION

Integrins comprise a family of cell adhesion receptors composed of alpha/beta heterodimeric subunits that provide a functional and structural bridge between the extracellular matrix and intracellular signaling molecules (Hynes R O, 1992). Expression of the αvβ6 integrin in ovarian cancers may contribute to the invasive potential of ovarian cancers (Ahmed N. et al., 2001; Ahmed N. et al., 2002) and expression of the αvβ6 integrin in colon cancer has been identified as an independent prognostic indicator for worse outcome in patients suffering from this disease (Bates R C. et al., 2005). The 15 mer amino acid sequence RSKAKWQTGTNPLYR (SEQ ID No. 1) located within the cytoplasmic tail of the β6 integrin subunit binds to extracellular signal-regulated kinase 2 (ERK2) and it has been proposed that this contributes to tumor growth (Ahmed N. et al., 2002).

The non-naturally occurring peptide RSKAKNPLYR (SEQ ID No. 2) derived from the β6 binding sequence has also been reported to inhibit cancer cell growth, which may be due at least in part to the inhibition of c-Src activity by the peptide (Agrez M V. et al., 2011).

Notably, within this sequence there is a NPxY/F (SEQ ID No. 3) motif common to β integrin cytoplasmic domains that forms part of a canonical recognition sequence for phosphotyrosine-binding (PTB) domains. Indeed, the NPxY/F (SEQ ID No. 3) motif is present in the amino acid sequences derived from the β2, β3 and β5 integrin subunits which correspond to the RSKAKNPLYR (SEQ ID No. 2) peptide, all of which have also been shown to be anti-cancer peptides and bind ERK2 (see International Patent Application WO 2005/037308) reflecting the apparent importance of the motif. PTB domains are protein modules present in a wide variety of signaling and cytoskeletal proteins. It has, for example, been suggested that phosphorylation of the tyrosine (Y) residue in the NPxY (SEQ ID No. 4) motif may represent a mode of regulating integrin interactions with other proteins at the cytoplasmic face of the plasma membrane (Takada Y. et al., 2007). The fundamental role of the highly conserved NPxY (SEQ ID No. 4) motif in regulating integrin-mediated function has been emphasized by Filardo and colleagues who showed that the NPxY (SEQ ID No. 4) motif within the β3 cytoplasmic tail is essential for αvβ3-dependent post-ligand binding events involved in cell migration and the metastatic phenotype of melanoma cells (Filardo E J, 1995).

SUMMARY OF THE INVENTION

The present invention relates to the unexpected finding that whilst the NPxY (SEQ ID No. 4) motif within the peptide RSKAKNPLYR (SEQ ID No. 2) derived from the β6 integrin subunit is essential for cancer cell growth inhibitory activity, modified forms of the peptide in which the NPxY (SEQ ID No. 4) motif and other amino acid residues except the charged amino acids arginine (R) and lysine (K) have been substituted for different amino acids, are essentially as effective at inhibiting cancer cell proliferation as the RSKAKNPLYR (SEQ ID No. 2) peptide itself. This surprising observation allows for the provision of a range of peptides to be synthesized which in at least some embodiments of the invention can inhibit the activity of a plurality of kinase enzymes involved in cellular activation pathways, providing new alternatives for the prophylaxis or treatment of cancer.

In particular, in an aspect of the invention there is provided an isolated or purified peptide for inhibiting growth of cancer cells, the peptide comprising the amino acid sequence RxKxKxxxxR (SEQ ID No. 5) wherein K and R are respectively lysine and arginine amino acid residues, each x is independently an amino acid, and the peptide has 50% or less amino acid sequence identity with the amino acid sequence RSKAKNPLYR (SEQ ID No. 2).

In at least some embodiments the peptide has 50% sequence identity with the amino acid sequence RSKAKNPLYR (SEQ ID No. 2). In other embodiments the peptide has 40% amino acid sequence identity with RSKAKNPLYR (SEQ ID No. 2).

The x amino acids in a peptide embodied by the invention may be the same or different to one another.

Typically, each x amino acid is independently an amino acid residue selected from the group consisting of alanine (A), valine (V), leucine (L), isoleucine (I), threonine (T), and serine (S) amino acid residues.

Typically, each x is independently a non-polar amino acid. More typically, each x amino acid is independently alanine (A) or valine (V).

In another aspect there is provided an isolated nucleic acid encoding a peptide embodied by the invention.

In another aspect there is provided an expression vector comprising nucleic acid encoding a peptide embodied by the invention for expression of the peptide in a cell.

A peptide or nucleic acid embodied by the invention can be coupled to a facilitator moiety for facilitating passage of the peptide or nucleic acid across the outer cell membrane of a cancer cell into the cell. However, this is not essential and various other methods for facilitating passage of the peptide or nucleic acid into the cell can be employed. Alternatively, a peptide embodied by the invention may have the inherent capacity to pass across the outer cell membrane into the cytoplasm of a cancer cell.

In another aspect there is provided an agent for inhibiting growth of a cancer cell, the agent comprising a peptide or nucleic acid embodied by the invention coupled to a facilitator moiety for facilitating passage of the peptide or nucleic across the outer cell membrane of the cancer cell into the cell.

In another aspect there is provided a pharmaceutical composition comprising a peptide, nucleic acid or agent embodied by the invention, together with a pharmaceutically acceptable carrier or excipient.

In another aspect there is provided a method for inhibiting the growth or proliferation of a cancer cell, comprising contacting the cell with an effective amount of a peptide, nucleic acid or agent embodied by the invention.

In another aspect of the invention there is provided a method for prophylaxis or treatment of cancer in a mammal, comprising administering to the mammal an effective amount of a peptide, nucleic acid or agent embodied by the invention.

In another aspect of the invention there is provided a method for prophylaxis or treatment of cancer in mammal, comprising treating the mammal with an effective amount of a peptide or agent embodied by the invention. It will be understood that the treatment may comprise administering an effective amount of a nucleic acid encoding the peptide for expression of the peptide in cancer cells of the mammal.

In another aspect there is provided a method for inhibiting activity of at least one protein kinase in a cell, comprising treating the cell with at least one peptide, nucleic acid or agent embodied by the invention.

Typically, the kinase is selected from the group consisting of c-Src and at least one kinase of the Akt non-specific serine/threonine protein kinase family.

Typically, the peptide inhibits the activity of at least one of Akt2 and Akt3 in the cell.

In another aspect there is provided a peptide, nucleic acid or agent embodied by the invention for use in the prophylaxis or treatment of cancer in a mammal.

In still another aspect of the invention there is provided the use of a peptide, nucleic acid or agent embodied by the invention in the manufacture of a medicament for prophylaxis or treatment of a cancer in a mammal.

The term "peptide" is used interchangeably herein with "polypeptide".

By the term "anti-cancer peptide" is meant a peptide which can inhibit growth and/or proliferation of cancer cells. In some embodiments, the peptide may be administered coupled to a facilitator moiety as described herein for facilitating entry of the peptide into a cancer cell.

By the term "cancer" is meant any type of malignant, unregulated cell proliferation. The cancer can be selected from the group consisting of, but is not limited to, epithelial cell cancers, carcinomas, sarcomas, lymphomas and blood cell cancers, including leukemias such as myeloid leukemias, eosinophilic leukemias and granulocytic leukemias.

The features and advantages of invention will become further apparent from the following detailed description of non-limiting embodiments.

BRIEF DESCRIPTION OF THE
ACCOMPANYING DRAWINGS

FIG. 1: Graph showing HT29 colon cancer cells cultured under serum-free conditions and exposed to peptide RSKAKNPLYR (SEQ ID No. 2) for 72 hours compared to peptides RKKR (SEQ ID No. 6), ASAAANPLYA (SEQ ID No. 7) and RKRK (SEQ ID No. 8).

Figure 2:
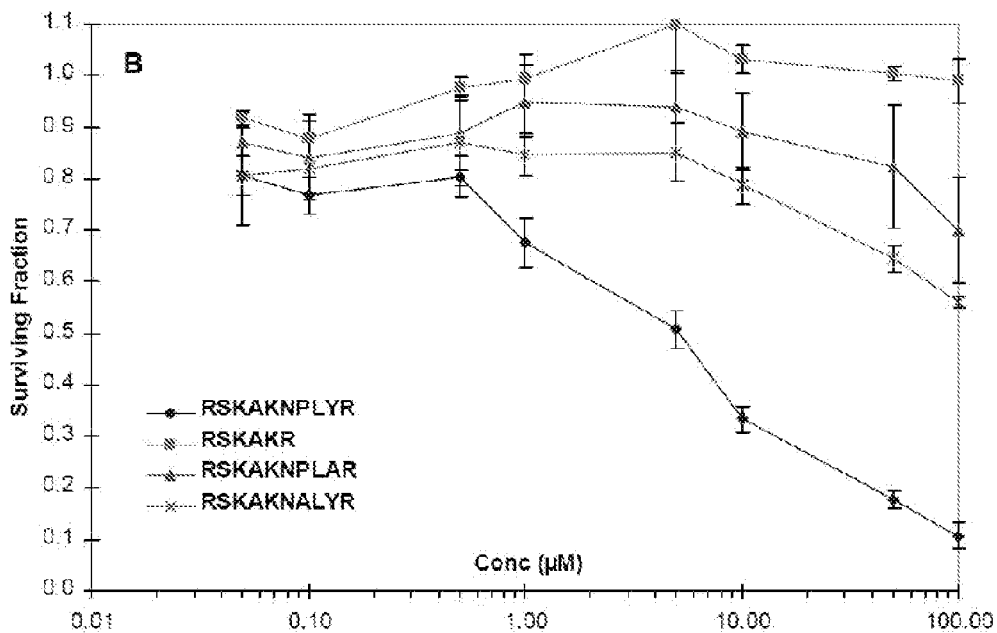

FIG. 2: Graph showing HT29 colon cancer cells cultured under serum-free conditions and exposed to peptide RSKAKNPLYR (SEQ ID No. 2) for 72 hours compared to peptides RSKAKR (SEQ ID No. 9), RSKAKNPLAR (SEQ ID No. 10) and RSKAKNALYR (SEQ ID No. 11).

Figure 3:
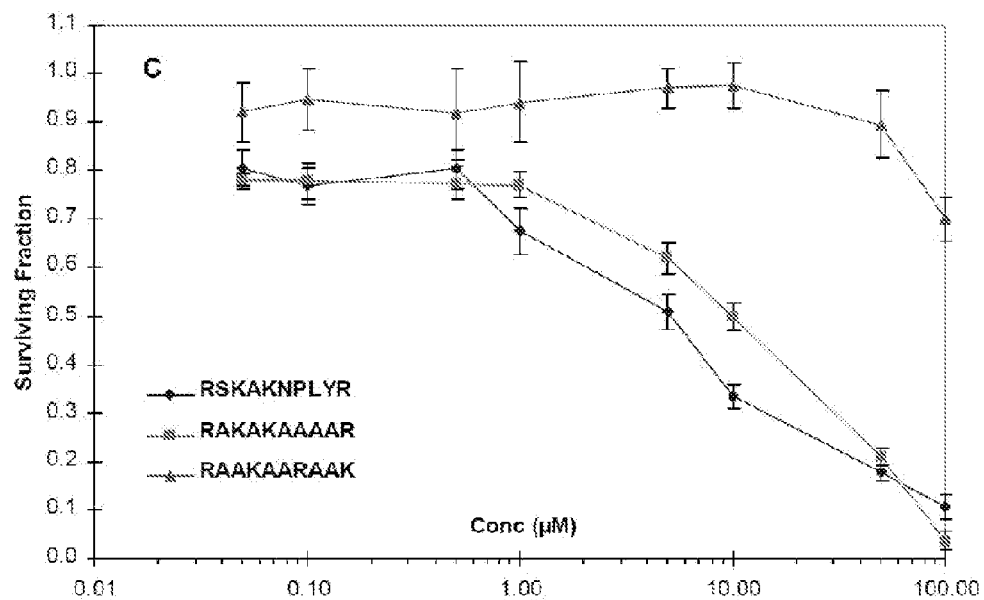

FIG. 3: Graph showing HT29 colon cancer cells cultured under serum-free conditions and exposed to peptide RSKAKNPLYR (SEQ ID No. 2) for 72 hours compared to peptides RAKAKAAAAR (10Ala) (SEQ ID No. 12) and RAAKAARAAK (scrambled 10Ala) (SEQ ID No. 13).

Figure 4:
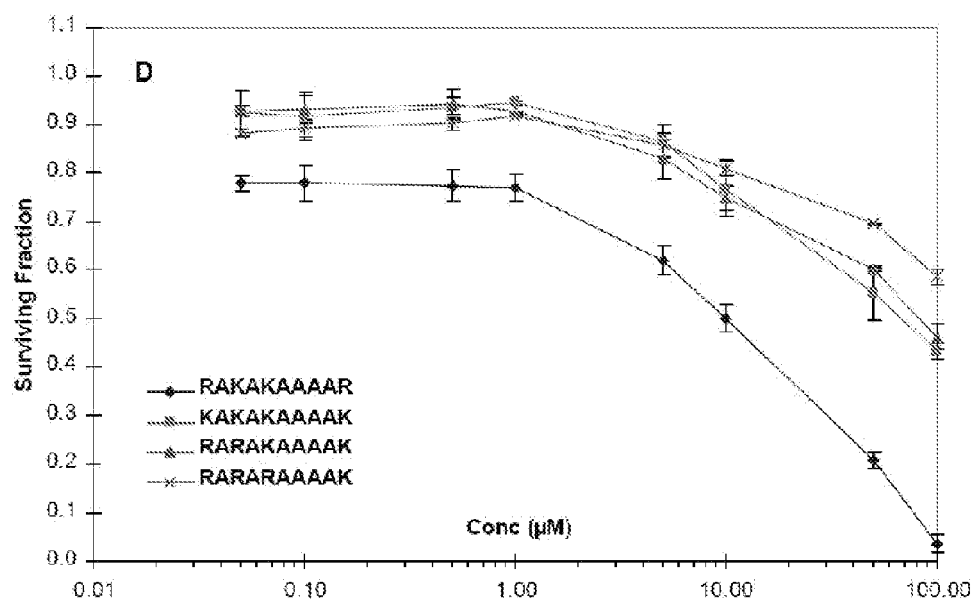

FIG. 4: Graph showing HT29 colon cancer cells cultured under serum-free conditions and exposed to peptides for 72 hours to peptide RAKAKAAAAR (10Ala) (SEQ ID No. 12) compared to peptides KAKAKAAAAK (SEQ ID No. 14), RARAKAAAAK (SEQ ID No. 15) and RARARAAAAR (SEQ ID No. 16).

Figure 5:
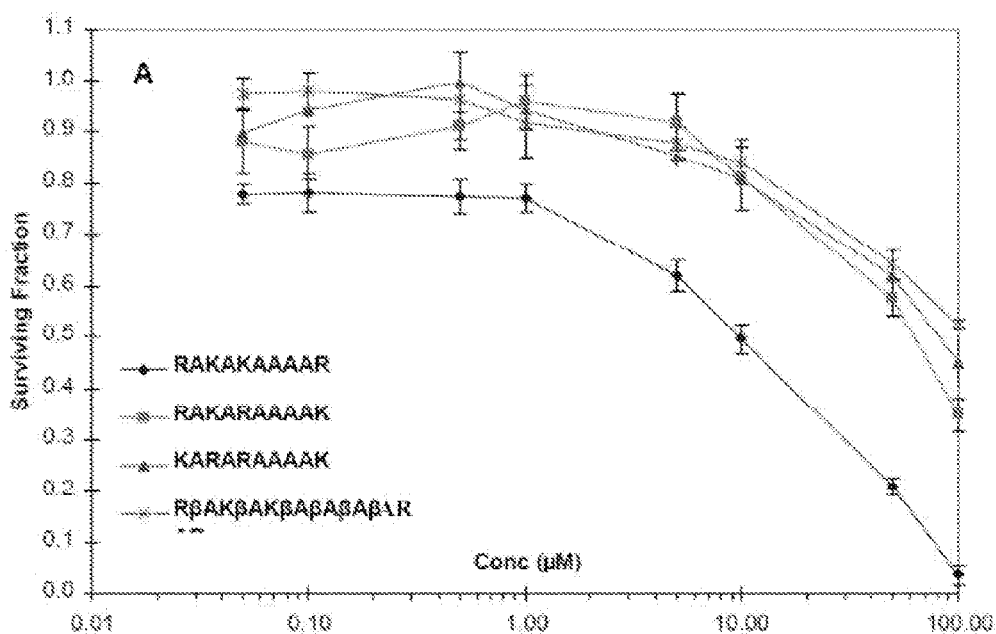

FIG. 5: Graph showing HT29 colon cancer cells cultured under serum-free conditions and exposed to peptide RAKAKAAAAR (10Ala) (SEQ ID No. 12) for 72 hours compared to peptides RAKARAAAAK (SEQ ID No. 17), KARARAAAAK (SEQ ID No. 18) and RβAKβAKβAβA-βAβAR) (SEQ ID No. 12).

Figure 6:
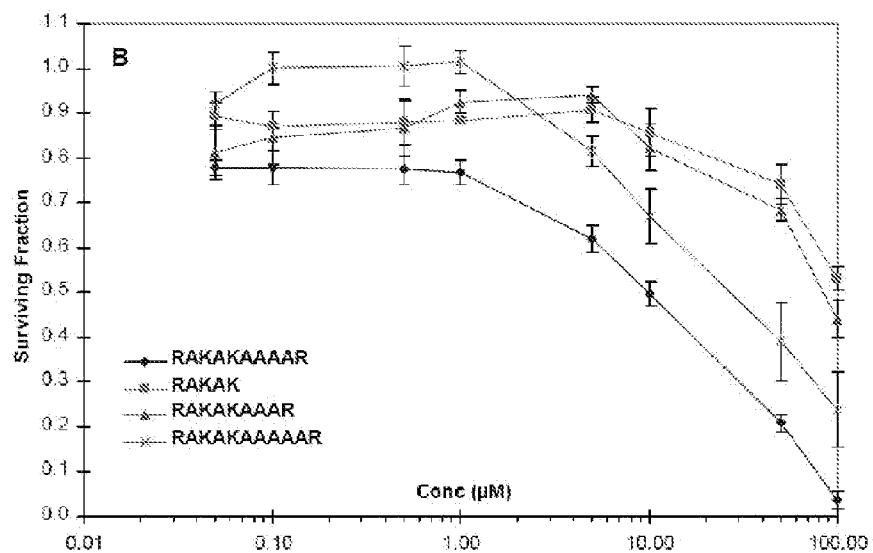

FIG. 6: Graph showing HT29 colon cancer cells cultured under serum-free conditions and exposed to peptide RAKAKAAAAR (10Ala) (SEQ ID No. 12) for 72 hours compared to peptides RAKAK (SEQ ID No. 19), RAKAKAAAR (SEQ ID No. 20) and RAKAKAAAAAR (SEQ ID No. 21).

Figure 7:
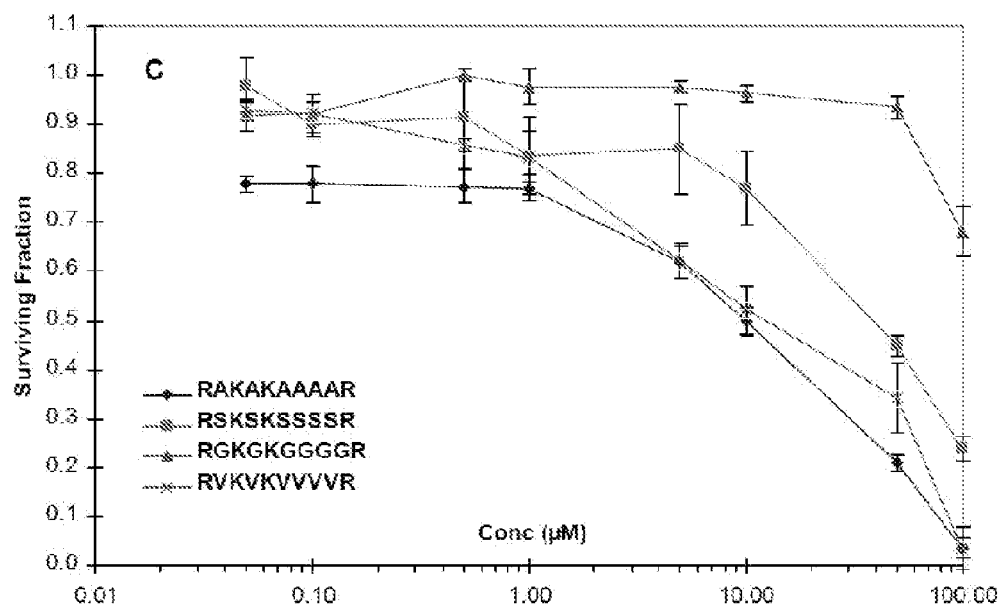

FIG. 7: Graph showing HT29 colon cancer cells cultured under serum-free conditions and exposed to peptide RAKA-KAAAAR (10Ala) (SEQ ID No. 12) for 72 hours compared to peptides RSKSKSSSSR (SEQ ID No. 22), RGKGKGGGGR (SEQ ID No. 23) and RVKVKVVVVR (SEQ ID No. 24).

Figure 8:
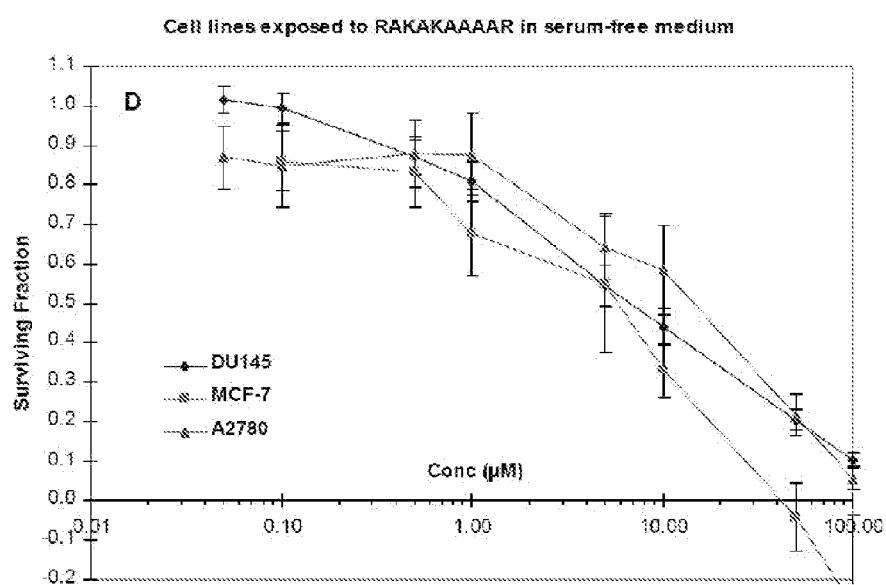

FIG. 8: Graph showing prostate (DU145), breast (MCF-7) and ovarian (A2780) cancer cell lines cultured under serum-free conditions and exposed to peptide RAKAKAAAAR (10 Ala) (SEQ ID No. 12) for 72 hours.

Figure 9:
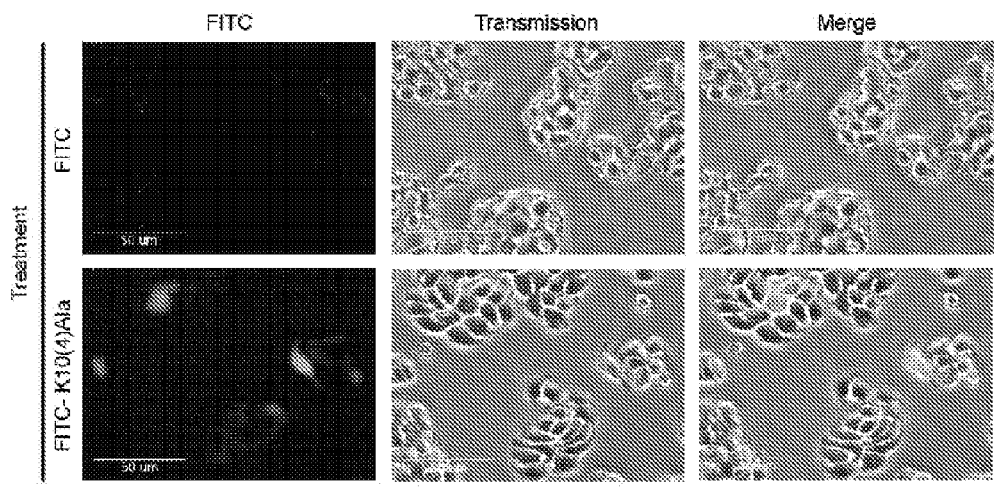

FIG. 9: Microphotographs showing internalization of FITC labeled peptide, FITC-KRAKAKAAAAR (FITC-K10 (4)Ala) (SEQ ID No. 25) by cancer cells.

Figure 10:
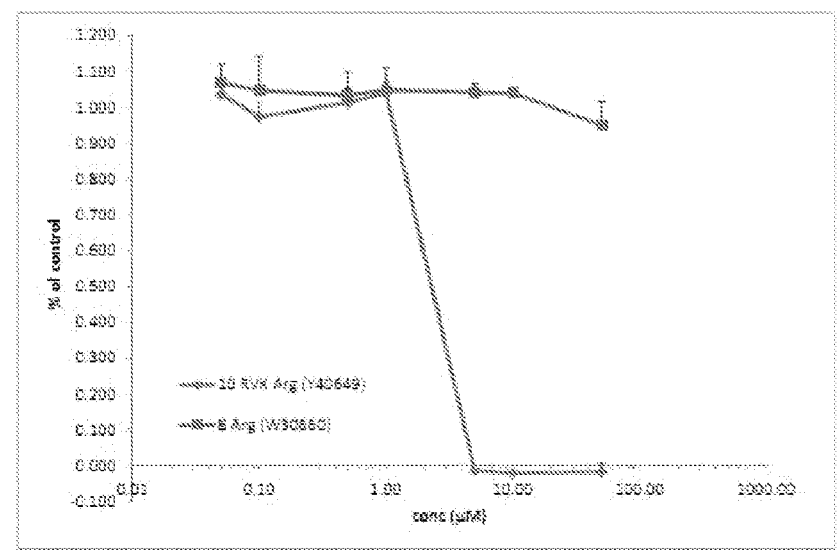

FIG. 10: Graph showing MDA468 breast cancer cells cultured in 5% serum containing medium and exposed to peptide RVKVKVVVVRRRRRRRRR (10 RVK Arg) (SEQ ID No. 26) for 48 hours verses an 8 mer polyarginine peptide.

Figure 11:
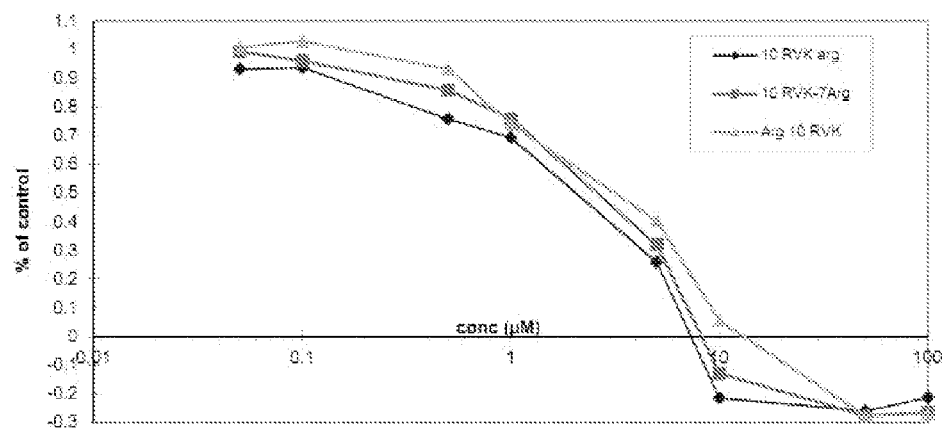

FIG. 11: Graph showing MDA468 breast cancer cells cultured in 5% serum containing medium and exposed to peptide RVKVKVVVVRRRRRRRRR (10 RVK Arg; solid diamonds) (SEQ ID No. 26), RVKVKVVVVRRRRRRR (10 RVK 7Arg; solid squares) (SEQ ID No. 27), or RRRRRRRRRVKVKVVVVR (Arg 10 RVK; solid triangles) (SEQ ID No. 28) for 48 hours.

Figure 12:
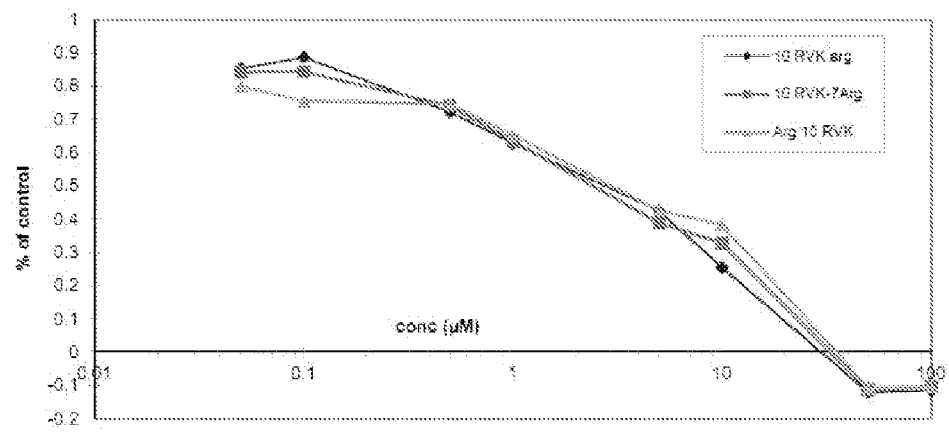

FIG. 12: Graph showing DU145 prostate cancer cells cultured in 5% serum containing medium and exposed to peptide RVKVKVVVVRRRRRRRRR (10 RVK Arg; solid diamonds) (SEQ ID No. 26), RVKVKVVVVRRRRRRR (10 RVK 7Arg; solid squares) (SEQ ID No. 27), or RRRRRRRRRVKVKVVVVR (Arg 10 RVK; solid triangles) (SEQ ID No. 28) for 48 hours.

DETAILED DESCRIPTION OF EXEMPLARY
EMBODIMENTS OF THE INVENTION

One of the major growth signalling pathways activated at the cell membrane through tyrosine kinase receptors is the PI3 kinase/Akt/mTOR pathway.

The serine/threonine Akt (also known as Protein Kinase B (PKB)) subfamily comprises three mammalian isoforms, Akt1, Akt2 and Akt3 (PKB alpha, PKB beta and PKB gamma, respectively). Akt functions as a cardinal nodal point for transducing extracellular (growth factor and insulin) and intracellular (receptor tyrosine kinases, Ras and Src) oncogenic signals. Moreover, ectopic expression of Akt, especially constitutively activated Akt, is sufficient to induce oncogenic transformation of cells and tumor formation in transgenic mice as well as chemoresistance (Cheng J Q. et al., 2005). Activated Akt is detectable and has been reported to be a poor prognostic factor for many types of cancer (Dennis P A, 2008). It has also been suggested that Akt3 may contribute to the more aggressive clinical phenotype characterized by estrogen receptor-negative breast cancers and androgen-insensitive prostate cancers (Nakatani K. et al., 1999). Indeed, Akt2 is thought to be essential for cell survival and important in malignant transformation, and elevated Akt2 levels have been identified in 32 of 80 primary breast carcinomas (Sun M. et al., 2001). Moreover, the Akt2 putative oncogene has been found to be amplified and over-expressed in some human ovarian and pancreatic carcinomas (Cheng J Q. et al., 1996).

Without being limited by theory, the anti-cancer activity of a peptide embodied by the invention may be at least partly due to capacity to inhibit at least some protein kinases in cancer cells. The peptide may inhibit the activity of the kinase(s) via direct interaction of the peptide with the kinase(s) or through indirect mechanism(s). However, the invention is not limited to the use of the peptides for the treatment of any particular type of cancer, and whether or not cells of the cancer exhibit an up-regulated level of activity of the kinase(s).

One or more of the amino acids of the amino acid sequence RxKxKxxxxR (SEQ ID No. 5) may be a β-amino acid, D-amino acid, or synthetic amino acid.

Moreover, each x amino acid in the amino acid sequence RxKxKxxxxR (SEQ ID No. 5) can be independently selected, and may be an amino acid not encompassed by the genetic code.

Typically, each x amino acid may be selected from the group consisting of alanine (A), valine (V), leucine (L), isoleucine (I), threonine (T) and serine (S) amino acid residues, but is not limited thereto.

Typically, each x amino acid is independently one with a terminal methyl group in a side chain attached to an a carbon (Cu) of the amino acid residue, such as an alanine (A), valine (V), leucine (L), isoleucine (I) or threonine (T) residue.

Typically, the RxKxKxxxxR peptide (SEQ ID No. 5) (which may be written as $Rx^1Kx^2Kx^3x^4x^5x^6R$) does not have a serine (S) or threonine (T) (both of which are polar amino acids) in position $x^1$.

Typically, the amino acid in position $x^6$ of the RxKxKxxxxR peptide (SEQ ID No. 5) is a non-polar amino acid selected from alanine (A), valine (V), leucine (L), or isoleucine (I).

Most typically, each x amino acid is independently a "non-polar" amino acid, selected from the above group.

In at least some embodiments, a peptide of the formula RxKxKxxxxR (SEQ ID No. 5) comprises only three different amino acids, namely arginine (R), lysine (K) and one other amino acid.

In particularly preferred embodiments, each x amino acid is independently alanine (A) or valine (V). In some embodiments, all of the x amino acids are alanine (A) residues whilst in other embodiments, the x amino acids are all valine (V) residues. In still further embodiments, the x amino acids are a mixture of alanine (A) and valine (V) amino acids.

When each x amino acid of the RxKxKxxxxR (SEQ ID No. 5) amino acid sequence is an alanine residue, the peptide will have 50% sequence identity with the RSKAKNPLYR (SEQ ID No. 2) peptide given that peptide already includes an alanine amino acid (underlined). In other instances, such as when all the x amino acids are valine, the peptide embodied by the invention will have 40% amino acid sequence identity with the RSKAKNPLYR (SEQ ID No. 2) peptide. Hence, a peptide as described herein may have 40% or 50% sequence identity with the RSKAKNPLYR (SEQ ID No. 2) peptide.

In at least some embodiments, a peptide embodied by the invention may comprise a dimer of the RxKxKxxxxR (SEQ ID No. 5) sequence. In some such embodiments, the dimer may be provided by the formation of a disulphide bridge between respective cysteine (C) residues added to the N-terminal end of each RxKxKxxxxR (SEQ ID No. 5) sequence whereby the dimer has the overall amino acid sequence RxxxxKxKxRC-s-s-CRxKxKxxxxR (SEQ ID No. 29), the disulphide bringe being indicated by -s-s-.

Further, in at least some embodiments, a peptide in accordance with the invention can have one or more positively charged amino acid residues coupled to the N- and/or C-terminal end of the peptide. For example, from 1 to 8 or more additional positively charged amino acids may be provided at the N- and/or C-terminal end of the RxKxKxxxxR (SEQ ID No. 5) peptide as discussed further below. The positively charged amino acids may, for instance, be independently selected from lysine, arginine and histidine. In at least some embodiments, each further positively charged amino acid is a lysine (K) residue. In other embodiments, a single such positively charged amino acid can be respectively coupled to the N- and/or C-terminal end of the peptide. The addition of the positively charged amino acid(s) (e.g., lysine) may facilitate linking of fluoro isothiocyanate (FITC) or other labels to the peptide.

The sequence identity between amino acid sequences as described herein can be determined by comparing amino acids at each position in the sequences when the sequences are optimally aligned for the purpose of comparison. Alignment of sequences can be performed using any suitable program or algorithm such as for instance, by the Needleman and Wunsch algorithm (Needleman and Wunsch, 1970). Computer assisted sequence alignment can be conveniently performed using standard software programs such as GAP which is part of the Wisconsin Package Version 10.1 (Genetics Computer Group, Madison, Wis., United States) using the default scoring matrix with a gap creation penalty of 50 and a gap extension penalty of 3. Other methods of alignment of sequences for comparison are also well known such as, but not limited to, the algorithms of Smith and Waterman, (1981) and Pearson and Lipman (1988), computerized implementation of such algorithms (e.g., BESTFIT, FASTA and BLAST), and by manual alignment and inspection of the sequences.

A peptide embodied by the invention can be provided by synthetic or recombinant techniques well known to the skilled addressee. Further, a peptide as described herein can incorporate an amino acid or amino acids not encoded by the genetic code, or amino acid analog(s). For example, a peptide embodied by the invention can include one or more D-amino acids rather than L-amino acids. Indeed, a peptide in accordance with the invention may consist partly or entirely of D amino acids. Accordingly, in some embodiments, the peptide(s) may include L-amino acids, D-amino acids or a mixture of L- and D-amino acids. The synthesis of peptides including D-amino acids can inhibit peptidase activity (e.g., endopeptidases) and thereby enhance stability and increase the half-life of the peptide in vivo compared to the corresponding L-peptide.

Likewise, the N-terminal and/or C-terminal ends of a peptide embodied by the invention can be modified to protect against or inhibit in vivo degradation by peptidases. For instance, the C-terminus of a peptide can be amidated to protect against peptidase degradation. The N- or C-terminal end of a polypeptide as described herein can alternatively (or as well) be pegylated with a plurality of ethylene glycol monomer units to render it more resistant to degradation by proteases in vivo or to inhibit their clearance from the circulation via the kidneys. Methods for pegylation of peptides are well known in the art and all such methods are expressly encompassed. Typically, a pegylated peptide used in a method embodied by the invention will be coupled to 2 or more monomer units of polyethylene glycol (PEG) and generally, from about 2 to about 11 monomers of PEG (i.e., (PEG)n where n equals from 2 to 11). Most usually, n will be 2.

A peptide embodied by the invention may be cyclised to provide enhanced rigidity and thereby stability in vivo and/or coupled with one or more moieties that improve solubility, lipophilic characteristics to enhance uptake by cells, stability or biological half-life, decreased cellular toxicity, or for instance to act as a label for subsequent detection or the like. A peptide as described herein may also result from post-translational or post-synthesis modification such as the attachment of carbohydrate moieties or chemical reaction(s) resulting in structural change(s) such as the alkylation or acetylation of amino acid residues or other changes involving the formation of chemical bonds.

In some embodiments, peptide dendrimers may be used for delivery of peptides to cancer cells in accordance with a method of the invention. Peptide dendrimers in at least some embodiments of the invention present units of a peptide in accordance with the invention coupled to a branched framework of polyamino acids (typically lysine branching units). The dendrimer will typically have at least 3 layers/generations of amino acid branching units, the units of the peptide embodied by the invention being coupled to the outermost layer/generation of the amino acid branching units such that the dendrimer presents at least 8 or more units of the peptide (e.g., 8, 9 or 10 or 12 units). The units of the peptide active of the invention presented by the dendrimer can be monomer units, multimer units and/or mixtures of monomer and multimer units of the peptide. Moreover, the dendrimer may be designed for release of the peptide(s) embodied by the invention in the cell cytoplasm. For example, the dendrimer framework may include sites for being cleaved or hydrolysed by protease enzyme(s) within the cell for release of the peptide(s) of the invention.

A peptide embodied by the invention can be bonded to the outermost layer/generation of polyamino acid branching units forming the framework of the dendrimer, or be synthetically assembled on the polyamino acid branching units of the dendrimer. The synthesis of dendrimers useful in one or more methods embodied by the invention can be achieved by divergent or convergent synthesis strategies. Suitable peptide dendrimer framework to which a polypeptide as described herein can be coupled, and methods for the provision of peptide dendrimers, are for example described in Lee et al, 2005; Sadler and Tam, 2002; and Cloninger, 2002, the entire contents of which are incorporated herein in their entirety by cross-reference. The peptide(s) presented by a dendrimer used in a method embodied by the invention may also be N- or C-terminal protected against proteolytic degradation (e.g., by amidation, pegylation or the like).

Peptidomimetics of peptides embodied by the invention are expressly encompassed herein. A peptidomimetic may, for example, comprise the substitution of one or more of the amino acids of a peptide embodied by the invention with an amino acid analogue wherein the amino acid analog(s) essentially do not diminish the anti-cancer activity of the parent peptide of the invention as may be assessed by MTT assay or the like.

Typically, a peptide embodied by the invention will have a length of about 60 amino acids or less. Usually, the peptide will have a length of up to about 50 amino acids, 45, 40, 35, 30, 25, 20 or 15 amino acids. For example, the peptide may have a length of 10, 11, 12, 13, 14, 15, 16, 17, 18, 19, 20, 21, 22, 23, 24 or 25 amino acids or more, e.g., up to 30, 35, 40, 45, 50 or 60 amino acids. However, it will be understood that peptides of all specific lengths and length ranges within those identified above are expressly encompassed (e.g., 10 to 12 amino acids, 10 to 13 amino acids, 10 to 14 amino acids, 10 to 15 amino acids, 10 to 16 amino acids, 10 to 17 amino acids, 10 to 18 amino acids, 10 to 19 amino acids, 10 to 20 amino acids, 10 to 21 amino acids, 10 to 22 amino acids, 10 to 22 amino acids, 10 to 23 amino acids, 10 to 24 amino acids, 10 to 25 amino acids, and the like).

Peptides in accordance with the invention or useful in a method embodied by the invention that are longer than 10 amino acids can be adapted for being cleaved within a cell for release of shorter peptides comprising the RxKxKxxxxR (SEQ ID No. 5) amino acid sequence. For example, a longer peptide may include an enzyme cleavage site for being cleaved for release of the shorter the RxKxKxxxxR (SEQ ID No. 5) sequence or an amino acid sequence which includes the RxKxKxxxxR (SEQ ID No. 5) sequence within a host or cancer cell. Chimeric proteins/polypeptides (i.e., fusion proteins) including a peptide embodied by the invention with or without an enzymatic cleavage site for release of the peptide at, or within, a cell are expressly provided for by the invention.

Peptides and fusion proteins embodied by the invention can be chemically synthesised or produced using conventional recombinant techniques. Nucleic acid encoding a fusion protein may for instance be provided by joining separate cDNA fragments encoding peptides having the desired amino acid sequence(s) by employing blunt-ended termini and oligonucleotide linkers, digestion to provide staggered termini as appropriate, and ligation of cohesive ends. Alternatively, PCR amplification of DNA fragments can be utilised employing primers which give rise to amplicons with complementary termini which can be subsequently ligated together.

Peptides and fusion proteins in accordance with the invention may be expressed in vitro and purified from cell culture for administration to the mammalian subject, or target cells (e.g., cancer cells) of the subject may be transfected with nucleic acid encoding the peptide or fusion protein for in vivo expression of the nucleic acid utilising the cellular transcription elements and translation ribosomal complexes of the host cell(s).

For expression of nucleic acid encoding a peptide or fusion protein embodied by the invention, the nucleic acid will typically first be introduced into a cloning vector and amplified in host cells, prior to the nucleic acid being excised and incorporated into a suitable expression vector(s) for transfection of cells. The expression vector may be designed for expression of the nucleic acid insert independently of genomic DNA of the host cell, or for site directed, homologous, or heterologous recombination into genomic DNA of the host cell for subsequent expression of the nucleic acid insert in the host cells.

Typical cloning vectors (e.g., cosmids) incorporate an origin of replication (ori) for permitting efficient replication of the vector, a reporter or marker gene for enabling selection of host cells transformed with the vector, and restriction enzyme cleavage sites for facilitating the insertion and subsequent excision of the nucleic acid sequence of interest. Preferably, the cloning vector has a polylinker sequence incorporating an array of restriction sites. The marker gene may be drug-resistance gene (e.g., $Amp^r$ for ampicillin resistance), a gene encoding an enzyme such as chloramphenicol acetyltransferase (CAT), β-lactamase, adenosine deaminase (ADA), aminoglycoside phosphotransferase (APH), dihydrofolate reductase (DHFR), hygromycin-B-phosphotransferase (HPH), thymidine kinase (TK), or for instance β-galactosidase encoded by the *E. coli* lacZ gene (LacZ'). Yeast reporter genes include imidazole glycerolphosphate dehydratase (HIS3), N-(5'-phosphoribosyl)-anthranilate isomerase (TRP1) and β-isopropylmalate dehydrogenase (LEU2). As will be appreciated, expression vectors of the invention may also incorporate such marker genes.

Cloning vectors that may be used include cloning vectors for mammalian, yeast and insect cells. Particular vectors that may find application include pBR322 based vectors and pUC vectors such as pUC118 and pUC119.

Suitable expression vectors include plasmids capable of expression of a DNA (e.g., genomic DNA or cDNA) insert. An expression vector will typically include transcriptional regulatory control sequences to which the inserted nucleic acid sequence is operably linked. By "operably linked" is meant the nucleic acid insert is linked to the transcriptional regulatory control sequences for permitting transcription of the inserted sequence without a shift in the reading frame of the insert. Such transcriptional regulatory control sequences include promoters for facilitating binding of RNA polymerase to initiate transcription, expression control elements for enabling binding of ribosomes to transcribed mRNA, and enhancers for modulating promoter activity. A promoter may be a tissue specific promoter which facilitates transcription of the nucleic acid insert only in specific cell lineages and not in other cell types or only to a relatively low level in such other cell types. The design of an expression vector will depend on the host cell to be transfected, the mode of transfection, and the desired level of transcription of the nucleic acid insert.

Numerous expression vectors suitable for transfection of prokaryotic (e.g., bacterial) or eukaryotic (e.g., yeast, insect or mammalian cells) are known in the art. Expression vectors suitable for transfection of eukaryotic cells include pSV2neo, pEF.PGK.puro, pTk2, pRc/CNV, pcDNAI/neo, non-replicating adenoviral shuttle vectors incorporating the polyadenylation site and elongation factor 1-α promoter and pAdEasy based expression vectors most preferably incorporating a cytomegalovirus (CMV) promoter. For expression in insect cells, baculovirus expression vectors may be utilised examples of which include pVL based vectors such as pVL1392, and pVL941, and pAcUW based vectors such as pAcUW1. Preferred expression vectors for expression of a nucleic acid insert in mammalian cells in accordance with embodiments of the invention include plasmids with a CMV or elongation factor 1α promotor such as pEF.PGK.puro (Huang, David C. S. et al., 1997). The pEF.PGK.puro plasmid contains an SV40 origin, EF-1α promoter, polycloning sites and a polyA region, and is particularly preferred for expression of a nucleic acid insert encoding a peptide or chimeric protein in accordance with the invention.

Intracellular delivery of peptides and nucleic acids embodied by the invention for prophylaxis or treatment of a cancer as described herein can be achieved utilising a "facilitator moiety" for facilitating passage or translocation of the peptide or nucleic acid across the outer cell/plasma membrane into the cytoplasm and/or nucleus of cells, such as a carrier peptide. A facilitator moiety as described herein may facilitate the entry of a peptide, agent or nucleic acid embodied by the invention into a cancer cell in any of a number of ways and the invention is not limited to any particular mechanism. The mechanism involved may, for example, comprise direct penetration into the cell (e.g., via enhanced cell membrane solubility or formation of a transient pore in the cell membrane), endocytosis-mediated cell entry (e.g., via interaction with cell a surface expressed receptor, or macropinocytosis), and cell entry via formation of a transitory structure on the cell membrane. The term "carrier peptide(s)" includes within its scope cell penetrating peptide(s) (CPPs). Carrier peptides that are known in the art include penetratin and variants or fragments thereof, human immunodeficiency virus Tat derived peptide, transportan derived peptide, cationic peptide (e.g., a polyarginine) (see further below), amphipathic peptides such as MPG and PEP-1 (e.g., see U.S. Pat. No. 6,841,535), signal peptides, and any suitable such peptide facilitator moiety can be employed. Particularly suitable signal peptides are described in U.S. Pat. No. 5,807,746 the contents of which are incorporated herein in its entirety. Signal peptide for Kaposi fibroblast growth factor (K-FGF) consisting of, or incorporating, the amino acid sequence AAVALLPAVLLALLA (SEQ ID No. 30) or AAVALLPAVLLALLAP (SEQ ID No. 31) are particular examples of carrier peptides that may be employed. Likewise, in at least some embodiments, the PEP-1 peptide may be utilised. It is not necessary that a carrier peptide used in a method of the invention be a complete peptide, and active fragments or modified or variant forms thereof which retain the ability to pass across the outer cellular membrane or otherwise translocate into target cells to effect delivery of the attached cargo peptide, nucleic acid or nucleic acid construct into the cytoplasm or nucleus of the cells may be utilised.

Rather than a carrier peptide, the facilitator moiety can be a lipid moiety or other non-peptide moiety (e.g., a carbohydrate moiety) which enhances cell membrane solubility of an anti-cancer peptide in accordance with the invention for passage across the outer cell membrane of the target cell or whereby entry of the peptide into the cell is facilitated. The lipid moiety can for instance be selected from triglycerides, including mixed triglycerides. Fatty acids and particularly, $C_{16}$-$C_{20}$ fatty acids can also be used. Typically, the fatty acid will be a saturated fatty acid and most usually, stearic acid. The invention is not limited to the use of any such non-peptide facilitator molecule, and any molecule that provides the desired cell membrane solubility and which is physiologically acceptable can be used.

In still another embodiment, a peptide embodied by the invention can be conjugated with a conjugation agent for forming a complex with a label, signalling, or other molecule (e.g., a contrast agent, imaging agent, biotin, streptavidin, radioisotope, fluorescent dye, chemiluminescent agent, chemiluminophore, bioluminescent agent, enzyme or binding fragment thereof (e.g., Fab and F(ab)$_2$ fragments), magnetic particle(s), etc) for detection of the peptide. As will be understood, a peptide embodied by the invention can be coupled to a facilitator moiety for facility passage of the peptide into a target cell and a conjugation agent complexed with, or for being complexed to, a label, signaling molecule, radioisotope or the like for detection of the peptide within the cell utilising a suitable imaging technique (e.g., magnetic resonance imaging (MRI)). DOTA (1,4,7,10-tetraazacyclodecane-1,4,7,10-tetraacetic acid) is an example of a conjugation agent that may be used and can be complexed to a range of compounds for use in cancer therapy and diagnosis such as monoclonal antibodies, radioisotopes, and metal cations (e.g., calcium and gadolinium). In a particularly preferred embodiment, a peptide embodied by the invention can be conjugated to DOTA complexed with gadolinium (Sturzu A et al, 2008) as a contrast agent for imaging of target cells.

In another embodiment, a peptide in accordance with the invention may be conjugated with gold nanoparticles typically 1-30 nm in size for imaging or for assisted cell death of the target cells through laser irradiation of branched gold particles. Gold nanoparticle transfer across plasma and nuclear membranes has been reported (de la Fuente J. M. and Berry C. C., 2005). However, a peptide embodied by the invention may be directly tagged with a label, signalling or other molecule (e.g., a radioisotope) for detection of the peptide or exertion of a therapeutic effect (e.g., cytotoxicity) on the target cancer cells.

A peptide or nucleic acid embodied by the present invention can be linked to the facilitator moiety (e.g., a peptide or dendrimer/dendrimer framework) and/or conjugation agent in any conventionally known manner such as by a respective linker. For instance, a peptide may be linked directly to a carrier peptide or dendrimer through an amino acid linker sequence by a peptide bond, or via a non-peptide covalent bond using a cross-linking reagent. A peptide or nucleic acid embodied by the invention may also be coupled to a facilitator moiety via electrostatic or hydrophobic interaction(s). For instance, "cargo" molecules that have a negative charge such as a nucleic acid as described herein may be linked to a carrier peptide or dendrimer by charge-association between negatively charged group(s) of the nucleic acid and positively charged amino acid(s) of the carrier peptide or an amino acid linker sequence. Chemical ligation methods may also be used to create a covalent bond between the carboxy terminal amino acid of the carrier peptide or a linker sequence and a peptide embodied by the invention. In the instance the agent comprises a nucleic acid encoding a peptide of the invention, a facilitator moiety as described herein may also facilitate passage of the nucleic acid through the nuclear membrane of eukaryotic cells into the nucleus of the cells. It has been reported, for instance, that delivery of DNA into mammalian cells is enhanced when complexed with a cell penetrating peptide (CPP) (Kim, H. H. et al., Int. J., 2007). Rapidly growing cancer cells commonly over-express cancer-specific receptors to enhance the up-take of nutrients or vitamins, and such intrinsic morphological and physiological differences between normal and cancer cells provide a means for targeted delivery of peptides, nucleic acids and agents embodied by the invention to cancer cells. In particular, targeting of cancer cells may be achieved by coupling a targeting moiety such as a ligand, a binding peptide, or an antibody or binding fragment thereof (such as Fab and $F(ab)_2$ fragments) that binds to a molecule expressed on the surface of the cells (e.g., a receptor such as EGFR) to the facilitator moiety (e.g., carrier peptide, dendrimer etc) or directly to the peptide, nucleic acid or agent (e.g., fusion protein, dendrimer etc.) embodied by the invention. Targeting moieties that may be utilised also include polyunsaturated fatty acids, transferrin, biotin, folic acid, and hyaluronic acid amongst others, see for instance, Ojima I. et al., 2012, the entire contents of which is incorporated herein by cross-reference.

One targeting approach in accordance with the invention employs coupling a facilitator moiety-peptide complex to an integrin receptor-targeted peptide which targets an extracellular integrin domain. For example, peptide linkers with the sequence DLXXL (SEQ ID No. 32) can be used to target the extracellular domain of the β6 integrin subunit. Given that ß6 expression enhances effective proteolysis at the cell surface by matrix metalloproteinase-9 (MMP-9) (Agrez M V et al, 1999), such targeting approaches may include engineering an MMP-9 or other MMP cleavage site between the targeting moiety and the facilitator moiety for release of the complex at the cell membrane and internalisation of the complex. As another example, the ligand recognition motif for αVβ6 integrin, RTDLDSLRTYTL (SEQ ID No. 33) may be used in conjunction with or without an engineered MMP (e.g., MMP-9) cleavage site to deliver a facilitator moiety-peptide complex as described herein to the surface of the target cell. Other targeting peptides with high affinity and selectivity for integrin αvβ6 may also be utilised such as NAVPNLRGDLQV-LAQKVART (SEQ ID No. 34) (Howard M. et al., 2007) which may be coupled directly to a peptide described herein again, with or without the provision of a MMP cleavage site.

It will be understood that a facilitator moiety may act to provide both targeted delivery to cancer cells in accordance with the invention as well as to facilitate entry of the attached cargo into the cells. That is, the same moiety may function in both roles. As such, the invention extends to complexes including only a facilitator moiety or a both a targeting moiety and a facilitator moiety.

Entry of the complex into a cell can occur via a number of mechanisms as described above, including via lysosomes which are rich in cathepsin. In this instance, the complex can include a cathepsin cleavage site for intracellular release of the cargo (e.g., peptide, nucleic acid or dendrimer embodied by the invention) from the complex to effect treatment of the cell. Various enzymatically cleavable and non-cleavable linkers are known in the art and one or more suitable independently selected such linker(s) may be utilised in the complex for effecting linkage to a targeting moiety and/or facilitator moiety in accordance with the invention. Suitable linkers besides those cleavable by cathepsin include linkers comprising cysteine residues providing a disulphide (—S—S—) bond cleaveable by an intracellular enzyme such as glutathione-S-transferase. In particularly preferred embodiments, the complex includes a linker for being cleaved or degraded intracellularly for release of a cargo peptide, nucleic acid or agent embodied by the invention within the cancer cell.

As another approach, bacterial derived minicells (e.g., De Boer P A, 1989)), liposomes, ghost bacterial cells, caveospheres, synthetic polymer agents, ultracentifuged nanoparticles and other anucleate nanoparticles may be loaded with dendrimers, peptides, nucleic acids or expression vectors (e.g., plasmids) in accordance with the invention and used for targeted delivery of the cargo to cancer cells (e.g., via bispecific antibodies, targeting peptides or the like on the minicell or liposome etc.) (e.g., see also MacDiarmid J. A. et al., 2007). Such shuttles may be formulated for injection, or oral consumption for passage through the acid environment of the stomach for release and uptake of the peptide, dendrimer or the like via the small intestine. Bacterial derived minicells loaded with a peptide embodied by the invention are particularly preferred for use in methods described herein.

Minicells are nano-sized cells that can be produced by mutations in gene(s) that control normal cell division and contain the cytoplasm and thereby cytoplasmic components for protein expression of the parent cell, but which are achromosomal and incapable of self-replication. The generation of minicells by derepressing (or upregulating) genes that control cell division has been shown to offer a solution to drug delivery to tumours at doses far less than would normally be used during intravenous infusion (MacDiarmid, J. A., et al., 2007). A minicell in the context of the present invention can be any achromosomal cell produced by aberrant cell division of the parent cell, as may result from pertubation or disturbance of the cell division process (e.g., binary fission) such as by genetic mutation(s) and/or inhibition of cellular components involved.

Minicells for use in a method as described herein can be prepared by any conventionally known method such as described in International patent application No. WO 03/033519, U.S. Pat. No. 7,183,105, and MacDiarmid, J. A., et al., 2007, the contents of all of which are expressly incorporated herein in their entirety by cross-reference. The inactivation of bacterial genes that control cell division to generate bacterial minicells is, for instance, further described in De Boer, P. A., et al., "A division inhibitor and a topological specificity factor coded for by the minicell locus determine placement of the division septum in *E. coli*". Cell 56, 1989, pp. 641-649. Methods for the purification of intact minicells utilising density gradient centrifugation (e.g., OptiPrep™, Axis-Shield PLC, Dundee, Scotland) and cross-flow filtration are described in U.S. Pat. No. 7,611,885 and U.S. Pat. No. 8,003,091, the contents of both of which are also expressly incorporated herein in their entirety by cross-reference.

Whilst minicells can result from down-regulated expression of genes involved in cell division, over-expression of some genes can also result in the production of minicells. Examples of bacterial cells from which minicells useful herein may be derived include bacteria such as *Eschererichia coli* (*E. coli*) (e.g., with mutations in MinA, MinB, cya, crp, MukA1, or MukeE, or which overexpress minB, minE, flsZ, sdi), *Bacillus subtilis* spp. (e.g., with mutations in minC, minD, ripX, or has smc mutations or OriC deletions), *Lacto-*

*bacillus* spp., *Neisseria gonorrhoeae* spp., *Salmonella* spp., (e.g., *Salmonella typhimurium*), *Helicobacter* spp; *Pseudomonas* spp., (e.g., *Pseudomonas aeruginosa*), Lysteria spp. (e.g., Lysteria *monocytogenes*) and *Campylobacter* spp. Bacteria may be Gram-positive (e.g., *L. monocytogenes*) or Gram-negative (e.g., *P. aeruginosa*). Mincells that have segregated from bacteria with porins in their outer membrane (i.e., normally Gram-negative bacteria although some Gram-positive bacteria also have porins) are particularly preferred for facilitating loading of the minicells with a peptide, nucleic acid, expression vector or other agent in accordance with the invention (or a mixture of ones of the foregoing) to be delivered to the target cells. Minicells may also be derived from archeabacteria or eukaryotic cells, e.g., see U.S. Pat. No. 7,183,105. Typically, however, bacterial derived minicells that is, minicells derived from bacterial parent cells, will be utilised.

Targeting of minicells to cancer cells may be obtained by the use of any suitable targeting moiety. The targeting moiety can be expressed on the surface of the minicell or, for example, minicells can be tagged or labelled with one or more selected targeting moieties. In particularly preferred embodiments, the targeting of minicells to tumour cells in that report may be achieved using a targeting moiety in the form of a bi-specific antibody complex that recognizes the O-antigen component of minicell surface lipopolysaccharide and a cell surface receptor specific for the mammalian cell to be targeted (e.g., EFGR), the two antibodies of the complex being linked together via their Fc regions with the use of protein A/G (see MacDiarmid, J. A., et al., 2007 and WO 03/033519. However, the invention is not limited thereto and other targeting moieties may be employed on the minicells. For example, the targeting moiety may comprise antibody binding fragment(s) rather than intact antibodies as described above. In other embodiments, a ligand, binding peptide or receptor specific for a binding partner on the target cells may be expressed on the outer surface of the minicell, and all suitable such alternatives are possible. The receptor expressed by the target cell(s) may be selected from hormone receptors, neurotransmitter receptors, receptor tyrosine kinase receptors, and G-protein linked receptors, amongst a large number of others. Minicells may be loaded with a peptide or nucleic acid (or other agent e.g., expression vector, dendrimer etc. in accordance with the invention) by passive diffusion via incubation of the minicells in an incubation medium containing the peptide, nucleic acid or other agent. To assist loading, the minicells may be rendered permeable to the agent(s) (e.g., by perforating the minicells) or the permeability of the minicells to the agent may otherwise be increased or enhanced using conventional techniques. Entry of the contents of the minicells into target cancer cells may be by translocation of the minicells into the target cells by phagocytosis (e.g., by neutrophils and macrophages) arising from interaction of the minicells with cell surface receptors expressed on the target cells or by endocytosis (either clathrin mediated or clathrin independent endocytosis), and subsequent degradation of the minicells and release of the contents of the minicells into the cytoplasm of the target cells (e.g., from intracellular compartments e.g., endosomes and/or lysosomes).

In at least some embodiments, a peptide embodied by the invention can also be linked to linked to a carbohydrate moiety e.g., glucose (D or L isomers) for the purpose of transport through LamB porins present on bacterial derived minicells. The porin superfamily contains a number of homotrimeric, transmembrane proteins that form water-filled pores across the outer cell membranes of Gram negative bacteria. Most porins form general, non-specific channels that are regulated by environmental changes. Maltoporin, also known as LamB porin, is responsible for the guided diffusion of maltose and maltodextrins into *E. coli* cells. In particular, LamB protein can also facilitate the diffusion of glucose (von Meyerburg K and Nikaido H, 1977) and glucose has been found to have the fastest rate of diffusion across LamB protein in vitro from a large range of sugars tested (Luckey M and Nikaido H, 1980).

Cationic peptides have also been used successfully to transfer macromolecules such as DNA and amino acid sequences into living cells. In embodiments in accordance with the invention, cationic peptides and other facilitator moieties as described herein may also be utilised to facilitate entry of peptides, nucleic acids and other agents into minicells and in the case of nucleic acids for instance, across the nuclear membrane. Examples of cationic peptides include polyarginine, polyhistidine, and polylysine peptides, and peptides consisting of a mixture of at least two of arginine, histidine and lysine amino acid residues. For example, a 15 mer arginine peptide has been reported to be the preferred number of amino acid residues to mediate expression of DNA encoding green fluorescent protein and the β-galactosidase gene in cancer cell lines (Choi H S. et al., 2003). It has also been reported that 9-35 mer cationic and/or amphipathic peptides are rapidly internalised across outer cell membranes (Bitler B. G. and Schroeder J. A., 2010). The invention extends to the use of such cationic peptides as facilitator moieties for facilitating the passage into the target cancer cells of a peptide embodied by the invention or nucleic acid (e.g., DNA) encoding the peptide for expression of the peptide within the cells. The cationic peptide can be of any suitable length for facilitating the entry of the peptide or nucleic acid into a target cell in accordance with a method embodied by the invention. Generally, the cationic peptide will be less than 20 amino acids in length and more usually, 15 amino acids in length or less. Typically, a cationic peptide for facilitating entry of a peptide embodied by the invention into a cell (e.g., the peptide RVKVKVVVVR (SEQ ID No. 24) will be from 2 to 10 amino acids in length and more generally, from 5 to 8 amino acids in length. When the cationic peptide is a polyarginine or polylysine it will preferably be about 8 amino acids length whereas a polyhistidine peptide will generally be about 5 amino acids in length. The cationic peptide can include L- and/or D-amino acids, and will generally be polyarginine peptide (i.e., a peptide comprised entirely of arginine residues). A cationic peptide can also increase solubility of a peptide of the invention in the instance the "x" amino acids of RxKxKxxxxR (SEQ ID No. 5) are, or are predominantly, non-polar amino acids (e.g., selected from alanine (A), valine (V), leucine (L) and isoleucine (I).

A respective independently selected cationic peptide can be coupled to the C-terminal and/or the N-terminal end of a peptide or to a nucleic acid embodied by the invention e.g., covalently such as by a peptide bond or via a linker In instances where a linker is utilised to link the cationic peptide to the peptide or nucleic acid, the linker can be an enzymatically cleavable linker as described above. Polyhistidine peptides may be used with or without a further facilitator moiety or carrier peptide such as polyarginine peptide, PEP-1 or TAT peptide, as the imidazole group of histidine may facilitate proton influx to endosomes leading to endosomal rupture and release of the cargo peptide or nucleic acid into the cytoplasm of the target cells. That is, the histidine residues may act as an endosomal escape agent (Liu, B. R. et al., 2011). This has applicability for delivery of peptides and nucleic acids to target cells utilising bacterial derived minicells as described above or via direct (non-encapsulated) delivery to target cells utilising a targeting moiety such as a monoclonal antibody specific for EGFR expressed by the target cells.

Various forms of expression vectors are known in the art as described above and any suitable such expression construct may be used for this purpose in accordance with the invention. Viral transfer methods can also be used for achieving the introduction of nucleic acids encoding a peptide or fusion protein embodied by the invention into a target cell (e.g., a cancer cell) either in vitro or in vivo. Suitable virus into which expression vectors may be packaged for delivery to target cells include adenovirus, vaccinia virus, retroviruses of avian, murine and human origin, herpes viruses including Herpes Simplex Virus (HSV) and EBV, papovaviruses such as SV40, and adeno-associated virus. Particularly preferred viruses useful in methods described herein include replication deficient recombinant adenovirus. Recombinant virus may be administered locally or systemically to achieve delivery of nucleic acid encoding a peptide or fusion protein into a target cell. Nucleic acid encoding a peptide or fusion protein in accordance with the invention may also be intracellularly delivered in vitro using conventional cold or heat shock techniques or for instance, calcium phosphate coprecipitation or electroporation protocols as are known in the art.

Transfected cells can be screened to identify cultures or cell lines that exhibit stable, reproducible expression of the nucleic acid insert and concomitant production of the peptide or fusion protein of the invention. Stable integration and expression of nucleic acids within a variety of host cells are well known in the art. Host cells that can be used for expression of polypeptides or fusion proteins include bacteria and probiotic bacteria such as *E. coli, B. subtilis, Lactococcus lactis, Streptomyces* and *Pseudomonas, Brevibacterium* and particularly B. linens bacterial strains, yeast such as *Sacchromyces* and *Pichia*, insect cells, avian cells and mammalian cells such as Chinese Hamster Ovary cells (CHO), COS, HeLa, HaRas, WI38, SW480, and NIH3T3 cells. The host cells are cultured in a suitable culture medium under conditions for facilitating expression of the introduced nucleic acid prior to purification of the expressed product from the host cells, and/or supernatants as the case may be using standard purification techniques.

Peptides and fusion proteins embodied by the invention can be purified from cell culture by sonication or disruption of cell membranes using detergents, centrifugation to remove membrane and solid fragments, and purification from solution or supernatant as applicable by affinity or immunoaffinity chromatography by methods known in the art. Suitable such solid substrates and supports that may be used include, but are not limited to agarose, sepharose and other commercially available supports (e.g., beads of latex, polystyrene, or dextran etc. Antibodies, binding fragments thereof or other suitable binding molecules for immobilizing the peptide or fusion protein of the invention on the solid support for subsequent elution and concentration therefrom can be bound to the solid substrate covalently utilizing commonly employed amide or ester linkers, or by adsorption. Peptides and fusion proteins in accordance with the invention can for example be expressed in host cells with a tag as is known in the art (e.g., poly-His (e.g., hexahistidine) tags) for aiding their purification. Where a tag such as poly-His is utilised the encoded peptide or fusion protein may further include suitable amino acid sequence that facilitates removal of the tag using endopeptidases (such additional amino acid sequence may not be provided if an N-terminal His-tag is used). Likewise, nucleic acid encoding a peptide or fusion protein in accordance with the invention may further include a signal peptide sequence for facilitating secretion of the peptide or fusion protein from a host cell for purification of the peptide or fusion protein by affinity chromatography as described above. Protocols for the preparation of solid substrates for immunoaffinity chromatography and affinity chromatography protocols are for instance described in Current Protocols in Molecular Biology—Ausubel F M. et al, Wiley-Interscience, 1988 and subsequent updates thereof.

Accordingly, peptides, fusion proteins, and nucleic acids in accordance with the invention can be provided in isolated or purified form. The term "purified" as used herein encompasses partial purification of the peptide, nucleic acid or agent of the invention, e.g., to a level of 80% purity or more, or at least 85%, 90%, 95%, 96%, 97%, 98%, or more (e.g., 99% or greater) as may be evaluated by electrophoretic and/or other techniques.

The toxicity profile of a peptide or agent embodied by the invention may be determined on cells by evaluation of cell morphology, trypan-blue exclusion, assessment of apoptosis and cell proliferation studies (e.g., cell counts, $^3$H-thymidine uptake and MTT assay).

Peptide(s) (e.g., including in dendrimer form), nucleic acids or other agents in accordance with the invention can be co-administered with anti-sense therapy or one or more conventional anti-cancer compounds or drugs. By "co-administered" is meant simultaneous administration in the same formulation or in two different formulations by the same or different routes, or sequential administration by the same or different routes whereby the peptide(s) and drugs exert their effect over overlapping therapeutic windows.

Conventional chemotherapeutic drugs which may be used in accordance with one or more embodiments of the invention can be selected from the group consisting of metal and non-metal based drugs. The metal complexes can be organic, inorganic, or mixed ligand co-ordination compounds or chelates. Transition metal complexes include for example complexes of platinum, palladium, copper, zinc, rhodium and ruthenium. Examples of platinum based chemotherapeutic drugs include cisplatin (cis-diamminedichloroplatinum (II)), oxaliplatin, ([Pt(1)xalto (1R), (2R)-diaminocyclohexane] complex), carboplatin (cis-diammine(1,1-cyclobutanedicarboxylato)platinum (II), and bleomycin. Examples of non-metal chemotherapeutic drugs include Paclitaxel, Gleevec, Docetaxel, Taxol, 5-fluorouracil, Doxorubicin, cyclophosphamide, Vincristine (Oncovin), Vinblastine, Vindesin, Camplothecin, Gemcitabine, Adriamycin, and topoisomerase inhibitors such as Irinotecan (CPT-11). Hence, a peptide embodied by the invention can be co-administered with one or more of such conventional anti-cancer drugs or other drugs.

In the instance a drug resistant cancer is being treated, a peptide or nucleic acid embodied by the invention may be co-administered to the mammalian subject in combination or in conjunction with the chemotherapeutic drug to which cells of the cancer are otherwise resistant. For example, inhibition of Src tyrosine kinase has been shown to enhance cytotoxicity of chemotherapeutic agents such as cisplatin in drug-sensitive ovarian cancer cells and to restore sensitivity in drug-resistant cells.

The Src family of cytoplasmic, membrane-associated non-receptor tyrosine kinases plays a significant role in the regulation of cellular activity. This family of kinases exert their effect upstream of mitogen activated protein (MAP) kinases and, hence, ERK activation. Phosphorylation by c-Src of targets occurs in a unidirectional manner and is initiated by interactions between c-Src and many membrane bound receptors and cellular factors near the plasma membrane as described above. As such c-Src and Src family members are critical mediators of multiple signaling pathways that regulate all stages of cancer progression (from initiation to metastasis) in multiple cell types. Inhibitors of c-Src that may be employed in a combination therapy in accordance with the invention include polypeptides, dendrimers and the like described International Patent Application No. PCT/AU2010/000203, the entire contents of which is incorporated herein by cross-reference. Examples of such c-Src inhibitors that may be utilised include the peptide RSKAKNPLYR (SEQ ID No. 2).

The cancer treated by a method of the invention may, for instance, be selected from the group consisting of carcinomas, sarcomas, lymphomas, solid tumors, head and neck cancers, blood cell cancers, leukaemias, myeloid leukaemias, eosinophilic leukaemias, granulocytic leukaemias, and cancer of the liver, tongue, salivary glands, gums, floor and other areas of the mouth, oropharynx, nasopharynx, hypopharynx and other oral cavities, oesophagus, gastrointestinal tract, stomach, small intestine, duodenum, colon, colonrectum, rectum, gallbladder, pancreas, larynx, trachea, bronchus, lung (including non-small cell lung carcinoma), breast, uterus, cervix, ovary, vagina, vulva, prostate, testes, penis, bladder, kidney, thyroid, bone marrow, and skin (including melanoma). Typically, the cancer will be an epithelium cancer and most usually, a non-dermal cancer. Most usually, the cancer will be selected from the group consisting of lung cancers, colon cancers, pancreatic cancers, breast cancers, colon adenocarcinomas and ovarian cancers.

A peptide, nucleic acid (e.g., an expression vector) or other agent (e.g., a fusion protein) embodied by the invention will typically be provided in a pharmaceutical composition comprising a pharmaceutically acceptable carrier and/or excipient for administration to the intended subject. In at least some embodiments, the peptide or other agent may be loaded into a bacterial derived minicell. The peptide, agent or pharmaceutical composition can be administered orally, intravenously, parenterally, rectally, subcutaneously, by infusion, topically such as in the treatment of skin cancers, intramuscularly, intraperitonealy, intranasaly, or any other route deemed appropriate. A pharmaceutical composition can, for example, be in the form of a liquid, suspension, emulsion, syrup, cream, ingestable tablet, capsule, pill, suppository, powder, troche, elixir, or other form that is appropriate for the selected route of administration.

Pharmaceutical compositions embodied by the invention include aqueous solutions. Injectable compositions will be fluid to the extent that syringability exists and typically, will normally be stable for a predetermined period to provide for storage after manufacture. Moreover, a pharmaceutically acceptable carrier may include any suitable conventionally known solvents, dispersion media, physiological saline and isotonic preparations or solutions, and surfactants. Suitable dispersion media can for example contain one or more of ethanol, polyols (e.g., glycerol, propylene glycol, liquid polyethylene glycol and the like), vegetable oils and mixtures thereof. For oral administration, any orally acceptable carrier can be used. In particular, the polypeptide can be formulated with an inert diluent, an assimilable edible carrier or it may be enclosed in a hard or soft shell gelatin capsule. Topically acceptable carriers conventionally used for forming creams, lotions or ointments for internal or external application can be employed. Such compositions can be applied directly to a site to be treated or via by dressings and the like impregnated with the composition.

A pharmaceutical composition as described herein can also incorporate one or more preservatives suitable for in vivo and/or topical administration such as parabens, chlorobutanol, phenol, sorbic acid, and thimerosal. In addition, prolonged absorption of the composition may be brought about by the use in the compositions of agents for delaying absorption such as aluminium monosterate and gelatin. Tablets, troches, pills, capsules and the like containing a peptide embodied by the invention can also contain one or more of the following: a binder such as gum tragacanth, acacia, corn starch or gelatin; a disintegrating agent such as corn starch, potato starch or alginic acid; a lubricant such as magnesium stearate; a sweetening agent such as sucrose, lactose or saccharin; and a flavouring agent.

The use of ingredients and media as described above in pharmaceutical compositions is well known. Except insofar as any conventional media or ingredient is incompatible with the dendrimer, use thereof in therapeutic and prophylactic compositions as described herein is included.

It is particularly preferred to formulate parenteral compositions in dosage unit form for ease of administration and uniformity of dosage. Dosage unit form as used herein is to be taken to mean physically discrete units suited as unitary dosages for the subject to be treated, each unit containing a predetermined quantity of at least one peptide embodied by the invention calculated to produce the desired therapeutic or prophylactic effect in association with the relevant carrier and/or excipient used. When the dosage unit form is for example, a capsule, tablet or pill, various ingredients may be used as coatings (e.g., shellac, sugars or both) to otherwise modify the physical form of the dosage unit or to facilitate administration to the subject.

A pharmaceutical composition will generally contain at least about 1% by weight of the peptide. The percentage may of course be varied and can conveniently be between about 5% to about 80% w/w of the composition or preparation. As will be understood, the amount of the peptide or other agent embodied by the invention in the composition will be such that a suitable effective dosage will be delivered to the subject taking into account the proposed route of administration. Preferred oral compositions embodied by the invention will contain between about 0.1 g and 15 g of the peptide.

The dosage of the peptide or other agent will depend on a number of factors including whether the peptide is to be administered for prophylactic or therapeutic use, the condition for which the peptide or agent is intended to be administered, the severity of the condition, the age of the subject, and related factors including weight and general health of the subject as may be determined by the physician or attendant in accordance with accepted principles. For instance, a low dosage may initially be given which is subsequently increased at each administration following evaluation of the individual's response. Similarly, the frequency of administration may be determined in the same way that is, by continuously monitoring the individual's response between each dosage and if necessary, increasing the frequency of administration or alternatively, reducing the frequency of administration.

Typically, a peptide embodied by the invention will be administered in accordance with a method described herein to provide a dosage of the polypeptide of up to about 100 mg/kg body weight of the individual, more usually in a range up to about 50 mg/kg body weight, and most usually in a range of about 5 mg/kg to 40 mg/kg body weight. In at least some embodiments, the peptide will be administered to provide a dosage of the peptide in a range of from about 5 to 25 mg/kg body weight, usually in a range of from about 5 mg/kg to about 20 mg/kg and more usually, in a range of from 10 mg/kg to about 20 mg/kg. When administered orally in dendrimer form, up to about 20 g of the dendrimer may be administered per day, (e.g., 4 oral doses per day, each dose comprising 5 g of the dendrimer).

With respect to intravenous routes, particularly suitable routes are via injection into blood vessels which supply a tumour or a cancer to be treated in a particular organ. In particular, the peptide, dendrimer, fusion protein or the like can be delivered into isolated organs, limbs and tissue by any suitable infusion or perfusion techniques. The peptide or other agent (e.g., an expression vector loaded in minicells) may also be delivered into cavities such for example the pleural or peritoneal cavity, or be injected directly into tumour tissue.

Suitable cloning and expression vectors useful in methods of the invention and methods for their preparation and delivery are described in manuals and handbooks well known to the skilled addressee, e.g., see Ausubel et al. (1994) Current Protocols in Molecular Biology, USA, Vol. 1 and 2, John Wiley & Sons, 1992; Sambrook et al (1998) Molecular cloning: A Laboratory Manual, Second Ed., Cold Spring Harbour Laboratory Press 1989, New York, and reprints and updates thereof, the contents of which are incorporated herein in their entirety by cross-reference. Likewise, suitable pharmaceutically acceptable carriers and formulations useful in compositions of the present invention can for instance, be found in handbooks and texts well known to the skilled addressee, such as "Remington: The Science and Practice of Pharmacy (Mack Publishing Co., 1995)", and any reprints and updates thereof. Methods and protocols for the transfection of cells and expression of nucleic acid inserts in vivo are for example described in WO 200631996, WO 200631689, WO 200629981, WO 200629005, US 20060063731, and US 20060063924, the contents of all of the foregoing publications, manuals and handbooks listed above are incorporated herein in their entirety by cross-reference.

The mammal can be any mammal treatable with a method of the invention. For instance, the mammal may be a member of the bovine, porcine, ovine or equine families, a laboratory test animal such as a mouse, rabbit, guinea pig, a cat or dog, or a primate or human being. Typically, the mammal is a human.

The present invention will be described herein after with reference to a number of non-limiting Examples.

Example 1

Cancer Cell Growth Inhibition Studies

1. Methods
1.1 Cell Lines and Culture Conditions

The human colon cancer cell line HT29, ovarian cancer cell line A2780, breast cancer cell lines MCF-7 and MDA468, and a prostate cancer cell line (DU145) were used for in vitro studies. The cell lines were cultured at 37° C., under air containing 5% $CO_2$ and passaged regularly for optimal growth. Cells were maintained in DMEM medium containing 10% fetal bovine serum. All culture medium preparations were further supplemented with penicillin/streptomycin (100 µg/ml), and 1.2 In Vitro Growth Inhibition MTT Assay Cells in logarithmic growth were transferred to 96-well plates in 100 µl of serum-containing medium at a density of 4000 cells per well. After 24 hours the previously added serum-containing medium was removed and 200 µl serum free medium (SFM) with or without peptide was added to each of triplicate wells. Drug exposure experiments were carried out on cell lines using varying concentrations of peptides (50 nM-100 µM) and cells were exposed to peptides for 72 hours in serum-free culture medium. Growth-inhibitory effects were evaluated by MTT (3-[4,5-dimethylthiazol-2-yl] 2,5-diphenyl-tetrazolium bromide) cell growth assay and absorbance was read at 540 nm. Growth of control cells was exponential during the whole incubation period. Mean surviving fractions±SEM values (minimum of 3 separate experiments) were determined for each peptide/cisplatin concentration.

1.3 c-Src Kinase Activity Assays

In vitro c-Src kinase activity assays were performed as per manufacture's instructions. Briefly, in a final reaction volume of 25 µL, c-Src (h) (5-10 mU) was incubated with 8 mM MOPS pH 7.0, 0.2 mM EDTA, 250 µM KVEKIGEGTYGV-VYK (SEQ ID No. 35) (Cdc2 peptide), 10 mM MgAcetate and [γ-33P-ATP](specific activity approximately 500 cpm/pmol). The reaction was initiated by the addition of the MgATP mix. After incubation for 40 minutes at room temperature, the reaction was stopped by the addition of 5 µL of a 3% phosphoric acid solution. 10 µL of the reaction was then spotted onto a P30 filtermat and washed three times for 5 minutes in 75 mM phosphoric acid and once in methanol prior to drying and scintillation counting.

1.4 Akt Kinase Activity Assays

In vitro PKB kinase activity assays were performed as per manufacture's instructions. Briefly, in a final reaction volume of 25 uL, PKB(h) (5-10 mU) was incubated with 8 mM MOPS pH 7.0, 0.2 mM EDTA, 30 uM of GRPRTSSFAE-GKK (SEQ ID No. 36), 10 mM Mg Acetate and [γ33P-ATP] (specific activity approximately 500 cpm/pmol, concentration as required). The reaction eas initiated by the addition of the MgATP mix. After incubation for 40 minutes at room temperature the reaction was stopped by the addition of 5 uL of a 3% phosphoric acid solution. 10 uL of the reaction mix was then spotted on to P30 filtermat and washed three times for 5 minutes in 75 mM phosphoric acid and once in methanol prior to drying and scintillation counting.

2. Results
2.1 Effect of Peptide Modifications on Cell Proliferation In Vitro.

A study was undertaken to determine whether loss of the NPLY (SEQ ID No. 37) motif or the loss of the charged amino acid residues (i.e., RKKR) within the RSKAKNPLYR (SEQ ID No. 2) peptide sequence (e.g., peptide sequence ASAAANPLYA) (SEQ ID No. 7) abrogated the cell growth-inhibitory effect of the full length RSKAKNPLYR (SEQ ID No. 2) peptide on proliferation of HT29 cells (Agrez et al., 2011).

As shown in FIG. 1, it was found that both the NPLY (SEQ ID No. 37) motif and the charged residues RKKR (SEQ ID No. 6) are necessary for the cell growth-inhibitory effect but each alone is not sufficient to inhibit cancer cell proliferation in vitro to the same degree as the full length 10 mer peptide RSKAKNPLYR (SEQ ID No. 2). A scrambled version of RKKR (SEQ ID No. 6) (i.e., RKRK) (SEQ ID No. 8) was significantly less effective at inhibiting growth of the cells at the highest peptide concentration of 100 uM (FIG. 1).

To further examine the requirement of the NPLY (SEQ ID No. 37) motif in inhibiting proliferation of HT29 cells the cells were exposed to a short variant of the 10 mer RSKAKN-PLYR (SEQ ID No. 2), namely RSKAKR (SEQ ID No. 9), which lacks the NPLY (SEQ ID No. 37) motif. As shown in FIG. 2, the RSKAKR (SEQ ID No. 9) peptide failed to inhibit proliferation of HT29 cells even at the highest concentration of 100 uM. Moreover, substitution of the specific residues proline and tyrosine by alanine within the NPLY (SEQ ID No.

37) motif abrogated the growth inhibitory effect seen in the presence of the parent 10 mer RSKAKNPLYR (SEQ ID No 2) (FIG. 2).

To further confirm that the NPLY (SEQ ID No. 37) motif was necessary to inhibit cancer cell growth, all non-charged residues within RSKAKNPLYR (SEQ ID No. 2) were replaced with alanine and the resulting peptide RAKA-KAAAAR (designated 10Ala) (SEQ ID No. 12) was tested for its effect on proliferation of HT29 cells. Surprisingly, as seen in FIG. 3, the ability of both peptides to inhibit cell growth was similar whereas a scrambled alanine-substituted peptide RAAKAARAAK (Scram 10Ala) (SEQ ID No. 13) was ineffective.

The growth inhibitory effect of the β6-derived peptide RSKAKNPLYR (SEQ ID No. 2) has previously been shown to be adversely affected in vitro in the presence of serum. This is thought to be due to the cleavage of amino acids from the amino terminus of RSKAKNPLYR (SEQ ID No. 2) (Agrez et al., 2011). In the present study 10Ala was similarly found to be adversely affected when tested in serum-containing medium (data not shown).

10 mer peptides derived from the 32 (i.e., KEKLKNPLFK) (SEQ ID No. 38), β3 (i.e., RARAKNPLYK) (SEQ ID No. 39), and 35 (i.e., RSRARNPLYR) (SEQ ID No. 40) integrin cytoplasmic domains that share significant homology with the β6-derived peptide RSKAKNPLYR (SEQ ID No. 2), have previously been reported to be also be effective at inhibiting proliferation of colon cancer cells in vitro (e.g., PCT/AU2010/000203). To determine whether the growth inhibitory effect of 10Ala would also be reflected by alanine-substituted homologs of these peptides, the non-charged residues of the β2, β3 and β5-derived peptides were substituted for alanine and examined for their effects on growth of HT29 cells. The resulting alanine (A) substituted peptides were as follows:

```
                                          (SEQ ID No. 14)
KAKAKAAAAK
(β2 derived alanine substituted peptide)

(SEQ ID No. 15)
RARAKAAAAK
(β3 derived alanine substituted peptide)

(SEQ ID No. 16)
RARARAAAAR
(β5 derived alanine substituted peptide)
```

As shown in FIG. 4, 10Ala was significantly more effective at inhibiting cell proliferation in vitro than any of the three alanine substituted peptides derived from the β2, β3 or β5 integrin cytoplasmic domains.

To determine whether the positions of arginine and lysine within 10Ala affected the ability of 10Ala to inhibit cancer cell growth, HT29 cells were cultured in the presence of 10Ala peptides in which the positions of one or both arginine and lysine residues had been inverted (RAKARAAAAK (SEQ ID No. 17) and KARARAAAAK (SEQ ID No. 18), respectively). As shown in FIG. 5, this significantly reduced the ability of the peptides to inhibit cell growth. Moreover, conversion of all alanine residues to the isomeric form of beta-alanine similarly reduced the ability of the peptide to inhibit growth of HT29 cells as shown in FIG. 5.

As shown in FIG. 6, shorter variants of 10Ala, i.e., RAKAK (SEQ ID No. 19) and RAKAKAAAR (SEQ ID No. 20), had minimal effect on the proliferation of HT29 cells whereas an 11 mer peptide which contained one extra alanine residue at the carboxy terminus was more effective than the shorter variants but still not as effective as 10Ala at inhibiting cell growth (FIG. 6).

To determine if the presence of alanine was a specific requirement for the growth inhibitory effect, the alanine residues within 10Ala were replaced with either valine (another non-polar amino acid) or serine and glycine (both polar amino acids). As shown in FIG. 7, replacement of alanine with glycine rendered the peptide ineffective except at the highest concentration whereas the serine substitute was more effective, albeit significantly less than 10 Ala. However, replacement of alanine residues with valine resulted in similar inhibition of growth of HT29 colon cancer cells as observed for 10Ala. The inhibitory effect of 10Ala on cell growth was also examined for other cancer cell types. As shown in FIG. 8, 10Ala was equally effective at inhibiting growth of human prostate (DU145), breast (MCF-7) and ovarian (A2780) cancer cell lines in vitro.

2.2 Uptake of 10Ala by Cancer Cells

The ability of 10 Ala to cross the plasma membrane of HT29 cells was assessed by means of confocal microscopy of cells exposed to 10Ala conjugated to fluoroscein isothiocyanate (FITC) under serum-free culture conditions. The peptide used in this study comprised the sequence KRAKA-KAAAAR (SEQ ID No. 25) (identified as FITC-K10(4)Ala) with an extra lysine residue at the amino terminus (to which the FITC label is attached). Many of the cells exhibited cytoplasmic localization of peptide after 24 hours in culture. A microphotograph showing localization of the FITC-labelled peptide to the cytoplasm of cells compared to cells treated with FITC alone is shown in FIG. 9.

2.3 Effect on Protein Kinase Activity

The ability of the β6 derived peptide RSKAKNPLYR (SEQ ID No. 2), RAKAKAAAAR (10Ala) (SEQ ID No. 12), RAAKAARAAK (Scram 10Ala) (SEQ ID No. 13), and the 10 mer valine substituted peptide RVKVKVVVVR (SEQ ID No. 24) to inhibit protein kinase activity was determined by means of cell-free in vitro kinase assays. As shown in Table 1, RAKAKAAAAR (SEQ ID No. 12) and RVKVKVVVVR (SEQ ID No. 24) had similar effects on c-Src activity as RSKAKNPLYR (SEQ ID No. 2) but in contrast to that peptide were markedly more effective at inhibiting Akt2 (PKB beta) and Atk3 (PKB gamma) activity whereas the scrambled version of 10Ala was essentially without effect.

TABLE 1

Inhibition of kinase activity

| Peptide (50 μM) | Inhibitory Activity (%) | | | No. of Experiments |
|---|---|---|---|---|
| | c-Src | Akt2 | Akt3 | |
| RSKAKNPLYR (10(4)) (SEQ ID No. 2) | 53 | 3 | 8 | 3 |
| RAKAKAAAAR (10(4) Ala) SEQ ID No. 12) | 27 | 0 | 52 | 3 |
| RAAKAARAAK (10(4) Ala scrambled) (SEQ ID No. 13) | 3 | 0 | 2 | 4 |
| RVKVKVVVVR (10RVK) SEQ ID No. 24) | 43 | 89 | 93 | 4 |

3. Discussion

Given the requirement for the NPLY (SEQ ID No. 37) motif and, in particular, the tyrosine (Y) and proline (P) residues within the β6-derived peptide RSKAKNPLYR (SEQ ID No. 2) to render the RSKAKNPLYR (SEQ ID No. 2) amino acid sequence effective at inhibiting cancer cell proliferation, it was completely unexpected to find that substitution of the NPLY (SEQ ID No. 37) motif with alanine residues including the amino-terminal serine (RAKAKAAAAR; designated 10Ala) (SEQ ID No. 12)) restored the inhibitory effect on cell proliferation that was not seen when cells were exposed to a deletion variant of RSKAKNPLYR (SEQ ID No. 2) that lacked the NPLY (SEQ ID No. 37) motif (i.e., RSKAKR) (SEQ ID No. 9) or variants with single alanine substitutions for either the proline or tyrosine residue within the NPLY (SEQ ID No. 37) motif (i.e., RSKAKNPLAR (SEQ ID No. 41) and RSKAKNALYR (SEQ ID No. 42), respectively).

This was all the more surprising as alanine is unlikely to bind strongly to a receptor given that it is a non-polar, hydrophobic amino acid with no opportunity for electrostatic interactions. In contrast, a scrambled version of 10Ala was ineffective as shown in FIG. 3, suggesting that the inhibitory effect of the 10Ala compound was determined by the spacing and sequence of the two arginine and two lysine residues.

Moreover, while β-alanine retains the same tetrahedral structure as alanine, the effect of insertion of β-alanines into 10Ala is to lengthen the backbone of the peptide which renders the peptide less effective at inhibiting cancer cell growth. Further to this, the peptides RAKAKAAAR (SEQ ID No. 20) (9 mer) and RAKAKAAAAAR (SEQ ID No. 21) (11 mer) that contained either 3 or 5 alanine residues between the lysine and the C-terminal arginine, respectively, were both found to be significantly less effective at inhibiting growth of colon cancer cells compared with 10Ala as shown in FIG. 6, confirming the relevance of length for the growth-inhibitory effect.

The lack of a relationship to integrin structure was further highlighted by the finding that replacement of the NPxY (SEQ ID No. 4) motif with alanine residues in the β6-derived sequence RSKAKNPLYR (SEQ ID No. 2) yielded an effective anticancer compound whereas alanine substitution of this motif in the respective integrin cytoplasmic domains of β2, β3 and β5 generated compounds that were relatively ineffective at inhibiting cell growth. In addition, 10Ala inhibits the growth-promoting kinase Akt3, unlike RSKAKNPLYR (SEQ ID No. 2), while still retaining substantial anti-Src activity (see Table 1). Moreover, 10RVK (RVKVKVVVVR) (SEQ ID No. 24) not only inhibits c-Src activity but is also very effective at inhibiting both Akt2 and Akt3 unlike the RSKAKNPLYR (SEQ ID No. 2) peptide as shown in Table 1. Taken together, these findings indicate that 10Ala and its related peptides cannot be classed as derivatives of β integrin cytoplasmic domains.

A major challenge in cancer therapy is the ability of tumor cells to escape the growth constraints imposed on a cell when targeting a single kinase. Among the signaling proteins that respond to a large variety of signals, Akt3 appears to be a central player in regulation of cell survival and proliferation making it an attractive therapeutic target for treatment of cancer. For example, Akt3 has been found to be over-expressed in breast and prostate cancers (Anderson et al., 1998) and in prostate cancer, the basal enzymatic activity of Akt3 has been found to be constitutively elevated and represents the major Akt isoform (Nakatani et al., 1999). Relevantly, inhibition of Akt3 has also recently been shown to result in reduction of VEGF resulting in less vascularised tumors in an ovarian xenograft mouse model (Liby et al., 2011).

Targeting Src kinases is also relevant in cancer therapy given that Src family kinases are required for the endomembrane activation of the growth-promoting Ras-MAPK pathway and c-Src activation has been documented in upwards of 50% of tumors drived from the colon, liver, lung, breast and pancreas (Bivona T. G et al., 2003). Accordingly, treatment with peptide embodied by the present invention and a c-Src inhibitor such as the β6 integrin-derived peptide RSKAKNPLYR (SEQ ID No. 2) may provide an effective combination cancer treatment.

In summary, novel anti-cancer peptides are provided herein which in preferred embodiments comprise only three different amino acids, are uniquely different from integrin-based peptides that have previously been reported to inhibit cancer cell growth.

Example 2

Inhibition of MDA468 Breast Cancer Cells

The growth inhibitory activity of various concentrations of the 10 RVK peptide (RVKVKVVVVR) (SEQ ID No. 24) with an 8 mer polyarginine sequence coupled to its C-terminal end (i.e., RVKVKVVVVRRRRRRRR (SEQ ID No. 26), referred to herein as 10 RVK Arg) on MDA468 breast cancer cells was assessed by a modified form of the MTT assay described in Example 1.2 in which 3000 cells per well were cultured for 48 hours in culture medium containing 5% serum. For the negative control, an 8 mer polyargine peptide (8 Arg) was used. The results shown in FIG. 10 are the average of 3 replicate wells for each dosage. As can be seen, the 10 RVK Arg peptide (solid diamonds) totally inhibited growth of the cancer cells at a concentration of from 5 μM to 50 μM whereas the 8 mer Arg peptide itself (solid squares) exhibited no effect at this concentration range.

In another study, the 10 RVK Arg peptide showed enhanced cell growth inhibitory activity compared to the 10 RVK peptide with penetratin coupled to its N-terminal (i.e., RQIKIWFQNRRMKWKKRVKVKVVVVR) (SEQ ID No. 43) in the treatment of MDA468 breast cancer cells at a concentration of from 5 μM to 10 μM and DU145 prostate cancer cells at a concentration of 10 μM to 50 μM as assayed by MTT assay (results not shown)

Example 3

Inhibition of and MDA468 Breast Cancer and DU145 Prostate Cancer Cells

The growth inhibitory activity of various concentrations of the 10 RVK Arg peptide on MDA468 breast cancer and DU145 prostate cancer cells was assessed by MTT assay involving incubating the cells in 5% serum containing medium for 48 hours as described in Example 2. As a comparison, inhibition of the growth of the cells by the 10 RVK peptide with a 7 mer polyarginine sequence coupled to its C-terminal end (i.e., RVKVKVVVVRRRRRRR (SEQ ID No. 27), referred to herein as 10 RVK 7 Arg) and the 10 RVK peptide with an 8 mer polyargine sequence coupled to its N-terminal end (i.e., RRRRRRRRRVKVKVVVVR (SEQ ID No. 28), referred to herein as Arg 10 RVK) were also assessed. The results for inhibition of the breast cancer cells are shown in FIG. 11 while the results for treatment of the prostate cancer cells are shown in FIG. 12. As can be seen, the peptides markedly inhibited growth of both of the breast and prostate cancer cells at concentrations of 0.5 μM or greater and showed a similar activity profile to one another.

Although a number of preferred embodiments have been described, it will be appreciated by persons skilled in the art that numerous further embodiments may be provided without departing from the invention. The present embodiments described are, therefore, to be considered in all respects as illustrative and not restrictive.

LITERATURE REFERENCES

1. Ahmed N, Niu J, Dorahy D J, Gu X, Andrews S, Meldrum C J, Scott R J, Baker M S, Macreadie I G, Agrez M V (2002) Direct integrin αvβ6-ERK binding: implications for tumour growth. Oncogene 21: 1370-1380.
2. Ahmed N, Pansino F, Clyde R, Murthi P, Quinn M A, Rice G E (2001), Overexpression of αvβ6 integrin in serous epithelial ovarian cancer regulates extracellular matrix degradation via the plasminiogen activation cascade. Carcinogenesis 23: 237-244.
3. Agrez, M. V., Gu, X., Turton, J., Meldrum, C., Niu, J., Antalis, T. and Howard, E. W., The αvβ6 integrin induces gelatinase B secretion in colon cancer cells. Int. J. Cancer 81, 90-97 (1999).
4. Agrez et al., Synergistic anti-tumour effect of cisplatin when combined with an anti-Src kinase integrin based peptide. J Cancer Therapy, 2(3); August 2011: doi: 10.4236/jct.2011.23039.
5. Anderson K E et al (1998) Translocation of PDK-1 to the plasma membrane is important in allowing PDK-1 to activate protein kinase B. Curr Biol 8: 684-691.
6. Bates R C, Bellovin D I, Brown C, Maynard E, Wu B, Kawakatsu H, (2005), Transcriptional activation of integrin β6 during the epithelial-mesenchymal transition defines a novel prognostic indicator of aggressive colon carcinoma. J Clin Invest 115: 339-347.
7. Bitler B. G. and Schroeder J. A., Recent Patents on Anticancer Drug Discovery, 2010, 5:99-108.
8. Bivona T G et al., Phospholipase C gamma activates Ras on the golgi apparatus by means of RasGRP1. Nature, Vol. 424: 694-698, 2003.
9. Cheng J Q, Ruggeri B, Klein W M, Sonoda G, Altomare D A, Watson D K, Testa J R (1996) Amplification of AKT2 in human pancreatic cancer cells and inhibition of AKT2 expression and tumorigenicity by antisense RNA. PNAS 93: 3636-3641.
10. Cheng J Q, Lindsley C W, Cheng G Z, Hua Y, Nicosia S V (2005) The AKT/PKB pathway: molecular target for cancer drug discovery. Oncogene 24: 7482-7492.
11. Choi H S, Kim H H, Yang J M and Shin S., An insight into the gene delivery mechanism of the arginine peptide system: Role of the peptide/DNA complex size. Biochimica et Biophysica Acta (BBA), 2006; 1760: 1604-1612.
12. Cloninger, M. J. Biological applications of dendrimers. Curr. Opin. Chem. Biology. 6, 742-748 (2002)
13. De Boer P A, Crossley, R E, and Rothfield, L I. A division inhibitor and topological specific factor coded for by the miicell locus determine proper placement of the division septum in E. coli. Cell, 56; 641-649, 1989.
14. de la Fuente J. M. and Berry C. C. Bioconjugate Chemistry, 2005, 16(5); ACS, pp 1176-1180.
15. Dehm S C and Bonham K. "Src gene expression in human cancer: The role of transcriptional activation. Biochem. Cell Biol. Vol. 82, 2: 263-274, 2004.
16. Dennis P A, Targeting Akt in Cancer: Promise, Progress, and Potential Pitfalls. AACR Education Book, 2008: 25-35.
17. Filardo E J, Brooks P C, Deming S L, Damsky C, CHeresh D A (1995) Requirement of the NPXY motif in the integrin beta 3 subunit cytoplasmic tail for melanoma cell migration in vitro and in vivo. J Cell Biol 130: 441-450.
18. Huang David, C S., Cory S and Strasser A., Oncogene (1997) 14:405-414.
19. Howard M, Dicara D, Marshall J F (2007) αvβ6 Peptide ligands and their uses. PCT. WO 2007/039728
20. Hynes R O. (1992) Integrins: versatility, modulation, and signaling in cell adhesion. Cell: 69: 11-25.
21. Kim H H, Lee W S, Yang J M and Shin S., Basic peptide system for efficient delivery of foreign genes. Biochimica et Biophysica Acta (BBA), 2003; 1640: 129-136.
22. Kim, H. H. et al., Int. J. Pharmaceutics, 2007, 335: 70-78
23. Lee, C. C., MacKay, J. A., Frechet, J. M. and Szoka, F. C. Designing dendrimers for biological applications. Nature Biotech. 23, 1517-1526 (2005).
24. Liby T A, Spyropoulos P, Lindner H B, Eldridge J, Beeson C, Hsu T, Muise-Helmericks R C (2011) Akt3 controls vascular endothelial growth factor secretion and angiogenesis in ovarian cancer cells. Cancer Cell Biol. DOI: 10.1002/ijc.26010.
25. Liu, B. R. et al., Biomaterials, 2011, 32:3520-3537
26. Luckey M and Nikaido H. Proc. Natl. Acad. Sci. USA Vol. 77: pp 167-171, (1980).
27. MacDiarmid, J A., Mugridge, N B., and Wiess, J C (2007), Cancer Cell; 11; 431-445.
28. Nakatani K, Thompson D A, Barthel A, Hiroshi S, Liu W, Weigel R J, Roth R A (1999) Upregulation of Akt3 in estrogen receptor-deficient and androgen independent prostate cancer cell lines. J Biol Chem 274: 21528-21532.
29. Needlemen, S. B., and Wunsch, C. C. A general method applicable to the search for similarities in the amino acid sequence of two proteins. J. Mol. Biol. 48(3), 443-53, 1970.
30. Ojima I. et al., Future Med Chem, 2012, 4(1):33-50.
31. Pearson, W R. And Lipman, D J. Proc. Natl. Acad. Sci. USA., 1988, April, 85(8):2444-2448.
32. Sadler, K. and Tam, J. P. Peptide dendrimers: applications and synthesis. Rev. Mol. Biotechnology. 90, 195-229, (2002).
33. Smith, T F. And Waterman, M S. J. Mol. Biol, 1981, 147(1) pp: 195-197.
34. Sun M, Paciga J E, Feldman R I, Yuan Z, Coppola D, Lu Y Y, Shelley S A, Nicosia S V, Cheng J Q (2001) Phosphotidylinositol-3-OH (PI3K)AKT2, activated in breast cancer, regulates and is induced by estrogen receptor α (ERα) via interaction between ERα and PI3K. Cancer Res 61: 5985-5991.
35. Takada Y et al. Protein family review—The integrins. Genome Biology, 2007; 8(5): 215.
36. von Meyerburg K and Nikaido H. Biochem Biophys Res. Vol. 78: pp 1100-1107, (1977).

The invention claimed is:

1. An isolated or purified peptide for inhibiting growth of cancer cells, the peptide comprising an amino acid sequence RxKxKxxxxR (SEQ ID No. 5) wherein K and R are respectively lysine and arginine amino acid residues, each x is independently an amino acid selected from the group consisting of alanine (A), valine (V), and serine (S), and the peptide has a length of from 10 to 40 amino acids.

2. The peptide according to claim 1 wherein each x is independently an amino acid selected from alanine (A) and valine (V).

3. The peptide according to claim 1 wherein each x is alanine (A).

4. The peptide according to claim 1 wherein each x is valine (V).

5. The peptide according to claim 1 wherein each x amino acid is independently selected from alanine (A) and valine (V).

6. The peptide according to claim 1 wherein each x amino acid is serine (S).

7. The peptide according to claim 1 wherein the peptide consists of the amino acid sequence RxKxKxxxxR (SEQ ID No. 5).

8. The peptide according to claim 1 wherein the peptide has a length of from 10 to 25 amino acids.

9. The peptide according to claim 1 wherein the peptide inhibits a kinase selected from the group consisting of c-Src and Akt non-specific serine/threonine protein kinases.

10. An agent for inhibiting growth and/or proliferation of a cancer cell, comprising a peptide as defined in claim 1 coupled to a facilitator moiety for facilitating passage of the peptide across the outer cell membrane of the cancer cell into the cytoplasm of the cell.

11. The agent according to claim 10 being a chimeric peptide.

12. An isolated nucleic acid encoding a peptide comprising an amino acid sequence RxKxKxxxxR (SEQ ID No. 5) wherein K and R are respectively lysine and arginine amino acid residues, each x is independently an amino acid selected from the group consisting of alanine (A), valine (V), and serine (S), and the peptide has a length of from 10 to 40 amino acids, wherein the peptide inhibits a kinase selected from the group consisting of c-Src and Akt non-specific serine/threonine protein kinases, or an agent as defined in claim 10 for expression of the peptide or agent.

13. An expression vector including a nucleic acid insert encoding a peptide as defined in claim 1 for expression of the peptide in a cell.

14. A pharmaceutical composition comprising a peptide comprising an amino acid sequence RxKxKxxxxR (SEQ ID No. 5) wherein K and R are respectively lysine and arginine amino acid residues, each x is independently an amino acid selected from the group consisting of alanine (A), valine (V), and serine (S), and the peptide has a length of from 10 to 40 amino acids, an agent as defined in claim 10, or a nucleic acid encoding a peptide comprising an amino acid sequence RxKxKxxxxR (SEQ ID No. 5) wherein K and R are respectively lysine and arginine amino acid residues, each x is independently an amino acid selected from the group consisting of alanine (A), valine (V), and serine (S), and the peptide has a length of from 10 to 40 amino acids for expression of the nucleic acid, together with a pharmaceutically acceptable carrier or excipient.

15. A pharmaceutical composition according to claim 14 further comprising bacterial-derived minicells loaded with the peptide.

16. A pharmaceutical composition according to claim 14 further comprising bacterial derived mini-cells loaded with the nucleic acid.

17. A method for inhibiting the growth and/or proliferation of a cancer cell, comprising treating the cell with an effective amount of a peptide comprising an amino acid sequence RxKxKxxxxR (SEQ ID No. 5) wherein K and R are respectively lysine and arginine amino acid residues, each x is independently an amino acid selected from the group consisting of alanine (A), valine (V), and serine (S), and the peptide has a length of from 10 to 40 amino acids, an agent as defined in claim 10, or a nucleic acid encoding a peptide comprising an amino acid sequence RxKxKxxxxR (SEQ ID No. 5) wherein K and R are respectively lysine and arginine amino acid residues, each x is independently an amino acid selected from the group consisting of alanine (A), valine (V), and serine (S), and the peptide has a length of from 10 to 40 amino acids for expression of the peptide in the cell.

18. A method for prophylaxis or treatment of cancer in a mammal, comprising administering to the mammal an effective amount of a peptide comprising an amino acid sequence RxKxKxxxxR (SEQ ID No. 5) wherein K and R are respectively lysine and arginine amino acid residues, each x is independently an amino acid selected from the group consisting of alanine (A), valine (V), and serine (S), and the peptide has a length of from 10 to 40 amino acids, an agent as defined in claim 10, or a nucleic acid encoding the peptide for expression of a peptide comprising an amino acid sequence RxKxKxxxxR (SEQ ID No. 5) wherein K and R are respectively lysine and arginine amino acid residues, each x is independently an amino acid selected from the group consisting of alanine (A), valine (V), and serine (S), and the peptide has a length of from 10 to 40 amino acids in cancer cells of the cancer.

19. A method for inhibiting activity of at least one protein kinase in a cell, comprising treating the cell with at least one peptide comprising an amino acid sequence RxKxKxxxxR (SEQ ID No. 5) wherein K and R are respectively lysine and arginine amino acid residues, each x is independently an amino acid selected from the group consisting of alanine (A), valine (V), and serine (S), and the peptide has a length of from 10 to 40 amino acids, an agent according to claim 10, or a nucleic acid encoding a peptide comprising an amino acid sequence RxKxKxxxxR (SEQ ID No. 5) wherein K and R are respectively lysine and arginine amino acid residues, each x is independently an amino acid selected from the group consisting of alanine (A), valine (V), and serine (S), and the peptide has a length of from 10 to 40 amino acids for expression of the nucleic acid in the cell.

20. The method according to claim 19 wherein the kinase is selected from the group consisting of c-Src and at least one kinase of the Akt non-specific serine/threonine protein kinase family.

21. The method according to claim 20 wherein the peptide inhibits the activity of at least one of Akt2 and Akt3.

* * * * *

SEQUENCE LISTING

<160> NUMBER OF SEQ ID NOS: 43

<210> SEQ ID NO 1
<211> LENGTH: 15
<212> TYPE: PRT
<213> ORGANISM: Homo sapiens

<400> SEQUENCE: 1

Arg Ser Lys Ala Lys Trp Gln Thr Gly Thr Asn Pro Leu Tyr Arg
1               5                   10                  15

<210> SEQ ID NO 2
<211> LENGTH: 10
<212> TYPE: PRT
<213> ORGANISM: artificial
<220> FEATURE:
<223> OTHER INFORMATION: Non naturally occurring peptide derived from
      the B6 binding sequence

<400> SEQUENCE: 2

Arg Ser Lys Ala Lys Asn Pro Leu Tyr Arg
1               5                   10

<210> SEQ ID NO 3
<211> LENGTH: 4
<212> TYPE: PRT
<213> ORGANISM: artificial
<220> FEATURE:
<223> OTHER INFORMATION: Motif common to B integrin cytoplasmic domains
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa is Tyrosine or Phenylalanine

<400> SEQUENCE: 3

Asn Pro Xaa Xaa
1

<210> SEQ ID NO 4
<211> LENGTH: 4
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid

<400> SEQUENCE: 4

Asn Pro Xaa Tyr
1

<210> SEQ ID NO 5
<211> LENGTH: 10
<212> TYPE: PRT
<213> ORGANISM: artificial
<220> FEATURE:
<223> OTHER INFORMATION: isolated or purified peptide for inhibiting
      growth of cancer cells
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

```
<220> FEATURE:
<221> NAME/KEY: misc_feature
<222> LOCATION: (6)..(9)
<223> OTHER INFORMATION: Xaa can be any naturally occurring amino acid

<400> SEQUENCE: 5

Arg Xaa Lys Xaa Lys Xaa Xaa Xaa Xaa Arg
1               5                   10

<210> SEQ ID NO 6
<211> LENGTH: 4
<212> TYPE: PRT
<213> ORGANISM: Artificial
<220> FEATURE:
<223> OTHER INFORMATION: Charged residues for growth inhibitory effect

<400> SEQUENCE: 6

Arg Lys Lys Arg
1

<210> SEQ ID NO 7
<211> LENGTH: 10
<212> TYPE: PRT
<213> ORGANISM: Artificial
<220> FEATURE:
<223> OTHER INFORMATION: peptide sequence without charged amino acid
      residues RKKR

<400> SEQUENCE: 7

Ala Ser Ala Ala Ala Asn Pro Leu Tyr Ala
1               5                   10

<210> SEQ ID NO 8
<211> LENGTH: 4
<212> TYPE: PRT
<213> ORGANISM: Artificial
<220> FEATURE:
<223> OTHER INFORMATION: A scrambled version of the charged residues
      RKKR

<400> SEQUENCE: 8

Arg Lys Arg Lys
1

<210> SEQ ID NO 9
<211> LENGTH: 6
<212> TYPE: PRT
<213> ORGANISM: ARTIFICIAL
<220> FEATURE:
<223> OTHER INFORMATION: SHORT VARIANT OF THE PEPTIDE FROM SEQUENCE 2

<400> SEQUENCE: 9

Arg Ser Lys Ala Lys Arg
1               5

<210> SEQ ID NO 10
<211> LENGTH: 10
<212> TYPE: PRT
<213> ORGANISM: artificial
<220> FEATURE:
<223> OTHER INFORMATION: A short variant peptide of sequence 2

<400> SEQUENCE: 10

Arg Ser Lys Ala Lys Asn Pro Leu Ala Arg
1               5                   10
```

```
<210> SEQ ID NO 11
<211> LENGTH: 10
<212> TYPE: PRT
<213> ORGANISM: artificial
<220> FEATURE:
<223> OTHER INFORMATION: short variant of sequence 2, scrambled

<400> SEQUENCE: 11

Arg Ser Lys Ala Lys Asn Ala Leu Tyr Arg
1               5                   10

<210> SEQ ID NO 12
<211> LENGTH: 10
<212> TYPE: PRT
<213> ORGANISM: artificial
<220> FEATURE:
<223> OTHER INFORMATION: B6 derived peptide
<220> FEATURE:
<221> NAME/KEY: MISC_FEATURE
<222> LOCATION: (11)..(11)
<223> OTHER INFORMATION: peptide with alanine and zero noncharged
      residues designated 10Ala.

<400> SEQUENCE: 12

Arg Ala Lys Ala Lys Ala Ala Ala Ala Arg
1               5                   10

<210> SEQ ID NO 13
<211> LENGTH: 10
<212> TYPE: PRT
<213> ORGANISM: Artificial
<220> FEATURE:
<223> OTHER INFORMATION: Scrambled peptide with Alanine in the place of
      all non-charged residues in peptide of sequence 2.
<220> FEATURE:
<221> NAME/KEY: MISC_FEATURE
<222> LOCATION: (10)..(10)
<223> OTHER INFORMATION: scrambled peptide with alanine in the place of
      all non-charged residues
<220> FEATURE:
<221> NAME/KEY: MISC_FEATURE
<222> LOCATION: (11)..(11)
<223> OTHER INFORMATION: scrambled peptide sequence having n as
      scrambled 10Ala

<400> SEQUENCE: 13

Arg Ala Ala Lys Ala Ala Arg Ala Ala Lys
1               5                   10

<210> SEQ ID NO 14
<211> LENGTH: 10
<212> TYPE: PRT
<213> ORGANISM: artificial
<220> FEATURE:
<223> OTHER INFORMATION: B2 derviced alanine substituted peptide

<400> SEQUENCE: 14

Lys Ala Lys Ala Lys Ala Ala Ala Ala Lys
1               5                   10

<210> SEQ ID NO 15
<211> LENGTH: 10
<212> TYPE: PRT
<213> ORGANISM: artificial
<220> FEATURE:
<223> OTHER INFORMATION: B3 derived alanine substituted peptide

<400> SEQUENCE: 15

Arg Ala Arg Ala Lys Ala Ala Ala Ala Lys
1               5                   10
```

```
<210> SEQ ID NO 16
<211> LENGTH: 10
<212> TYPE: PRT
<213> ORGANISM: artificial
<220> FEATURE:
<223> OTHER INFORMATION: B5 derived alanine substituted peptide

<400> SEQUENCE: 16

Arg Ala Arg Ala Arg Ala Ala Ala Ala Arg
1               5                   10

<210> SEQ ID NO 17
<211> LENGTH: 10
<212> TYPE: PRT
<213> ORGANISM: artificial
<220> FEATURE:
<223> OTHER INFORMATION: 10Ala peptide wherein the position of one or
      both arginine and lysine residues have been inverted

<400> SEQUENCE: 17

Arg Ala Lys Ala Arg Ala Ala Ala Ala Lys
1               5                   10

<210> SEQ ID NO 18
<211> LENGTH: 10
<212> TYPE: PRT
<213> ORGANISM: artificial
<220> FEATURE:
<223> OTHER INFORMATION: 10Ala peptide in which the positions of one or
      both arginine and lysine residues have been inverted

<400> SEQUENCE: 18

Lys Ala Arg Ala Arg Ala Ala Ala Ala Lys
1               5                   10

<210> SEQ ID NO 19
<211> LENGTH: 5
<212> TYPE: PRT
<213> ORGANISM: artificial
<220> FEATURE:
<223> OTHER INFORMATION: shorter variant of 10Ala

<400> SEQUENCE: 19

Arg Ala Lys Ala Lys
1               5

<210> SEQ ID NO 20
<211> LENGTH: 9
<212> TYPE: PRT
<213> ORGANISM: artificial
<220> FEATURE:
<223> OTHER INFORMATION: short variant of 10Ala

<400> SEQUENCE: 20

Arg Ala Lys Ala Lys Ala Ala Ala Arg
1               5

<210> SEQ ID NO 21
<211> LENGTH: 11
<212> TYPE: PRT
<213> ORGANISM: artificial
<220> FEATURE:
<223> OTHER INFORMATION: variant peptide of 10Ala having 5 alanine
      residues between the lysine and the C-terminal arginine

<400> SEQUENCE: 21

Arg Ala Lys Ala Lys Ala Ala Ala Ala Ala Arg
1               5                   10
```

```
<210> SEQ ID NO 22
<211> LENGTH: 10
<212> TYPE: PRT
<213> ORGANISM: artificial
<220> FEATURE:
<223> OTHER INFORMATION: peptide

<400> SEQUENCE: 22

Arg Ser Lys Ser Lys Ser Ser Ser Ser Arg
1               5                   10

<210> SEQ ID NO 23
<211> LENGTH: 10
<212> TYPE: PRT
<213> ORGANISM: artificial
<220> FEATURE:
<223> OTHER INFORMATION: peptide

<400> SEQUENCE: 23

Arg Gly Lys Gly Lys Gly Gly Gly Gly Arg
1               5                   10

<210> SEQ ID NO 24
<211> LENGTH: 10
<212> TYPE: PRT
<213> ORGANISM: artificial
<220> FEATURE:
<223> OTHER INFORMATION: peptide

<400> SEQUENCE: 24

Arg Val Lys Val Lys Val Val Val Val Arg
1               5                   10

<210> SEQ ID NO 25
<211> LENGTH: 11
<212> TYPE: PRT
<213> ORGANISM: artificial
<220> FEATURE:
<223> OTHER INFORMATION: FITC-K10(4)Ala having an extra lysine residue
      at the amino terminus

<400> SEQUENCE: 25

Lys Arg Ala Lys Ala Lys Ala Ala Ala Ala Arg
1               5                   10

<210> SEQ ID NO 26
<211> LENGTH: 18
<212> TYPE: PRT
<213> ORGANISM: artificial
<220> FEATURE:
<223> OTHER INFORMATION: 8 mer polyarginine sequence couple to the
      C-terminal end of 10 RVK peptide

<400> SEQUENCE: 26

Arg Val Lys Val Lys Val Val Val Val Arg Arg Arg Arg Arg Arg
1               5                   10                  15

Arg Arg

<210> SEQ ID NO 27
<211> LENGTH: 17
<212> TYPE: PRT
<213> ORGANISM: artificial
<220> FEATURE:
<223> OTHER INFORMATION: 10RVK peptide with a 7 mer polyarginine
      sequence coupled to its C-terminal end
```

-continued

```
<400> SEQUENCE: 27

Arg Val Lys Val Lys Val Val Val Arg Arg Arg Arg Arg Arg Arg Arg
1               5                   10                  15

Arg

<210> SEQ ID NO 28
<211> LENGTH: 18
<212> TYPE: PRT
<213> ORGANISM: artificial
<220> FEATURE:
<223> OTHER INFORMATION: 10 RVK peptide with an 8 mer polyargine
      sequence coupled ot its N-terminal end

<400> SEQUENCE: 28

Arg Arg Arg Arg Arg Arg Arg Arg Val Lys Val Lys Val Val Val
1               5                   10                  15

Val Arg

<210> SEQ ID NO 29
<211> LENGTH: 22
<212> TYPE: PRT
<213> ORGANISM: Artificial
<220> FEATURE:
<223> OTHER INFORMATION: Peptide comprising a dimer of sequence 5 having
      a disulphide bridge between the cysteine residues added to the
      N-terminal end of each of sequence 5.
<220> FEATURE:
<221> NAME/KEY: MISC_FEATURE
<223> OTHER INFORMATION: disulphide bond between the cysteine residues
      added to the N-terminal of each.
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(21)
<223> OTHER INFORMATION: Xaa can be any naturally occurring amino acid

<400> SEQUENCE: 29

Arg Xaa Xaa Xaa Xaa Lys Xaa Lys Xaa Arg Cys Cys Arg Xaa Lys
1               5                   10                  15

Xaa Lys Xaa Xaa Xaa Xaa Arg
                20

<210> SEQ ID NO 30
<211> LENGTH: 15
<212> TYPE: PRT
<213> ORGANISM: artificial
<220> FEATURE:
<223> OTHER INFORMATION: an amino acid sequence from signal peptide for
      Kaposi fibroblast growth factor
```

```
<400> SEQUENCE: 30

Ala Ala Val Ala Leu Leu Pro Ala Val Leu Leu Ala Leu Leu Ala
1               5                   10                  15

<210> SEQ ID NO 31
<211> LENGTH: 16
<212> TYPE: PRT
<213> ORGANISM: artificial
<220> FEATURE:
<223> OTHER INFORMATION: amino acid of signal peptide for K-FGF

<400> SEQUENCE: 31

Ala Ala Val Ala Leu Leu Pro Ala Val Leu Leu Ala Leu Leu Ala Pro
1               5                   10                  15

<210> SEQ ID NO 32
<211> LENGTH: 5
<212> TYPE: PRT
<213> ORGANISM: artificial
<220> FEATURE:
<223> OTHER INFORMATION: peptide linker to target the extracellular
      domain of the B6 integrin subunit
<220> FEATURE:
<221> NAME/KEY: misc_feature
<222> LOCATION: (3)..(4)
<223> OTHER INFORMATION: Xaa can be any naturally occurring amino acid

<400> SEQUENCE: 32

Asp Leu Xaa Xaa Leu
1               5

<210> SEQ ID NO 33
<211> LENGTH: 12
<212> TYPE: PRT
<213> ORGANISM: Artificial
<220> FEATURE:
<223> OTHER INFORMATION: Ligand recognition motif for alphaVB6 integrin

<400> SEQUENCE: 33

Arg Thr Asp Leu Asp Ser Leu Arg Thr Tyr Thr Leu
1               5                   10

<210> SEQ ID NO 34
<211> LENGTH: 20
<212> TYPE: PRT
<213> ORGANISM: artificial
<220> FEATURE:
<223> OTHER INFORMATION: Targeting peptide with high affinity for
      integrin alphavB6.

<400> SEQUENCE: 34

Asn Ala Val Pro Asn Leu Arg Gly Asp Leu Gln Val Leu Ala Gln Lys
1               5                   10                  15

Val Ala Arg Thr
            20

<210> SEQ ID NO 35
<211> LENGTH: 15
<212> TYPE: PRT
<213> ORGANISM: Artificial
<220> FEATURE:
<223> OTHER INFORMATION: Cdc2 peptide

<400> SEQUENCE: 35

Lys Val Glu Lys Ile Gly Glu Gly Thr Tyr Gly Val Val Tyr Lys
1               5                   10                  15
```

```
<210> SEQ ID NO 36
<211> LENGTH: 13
<212> TYPE: PRT
<213> ORGANISM: Artificial
<220> FEATURE:
<223> OTHER INFORMATION: Peptide for PKB kinase activity assays per
      manufaturer's instructions.

<400> SEQUENCE: 36

Gly Arg Pro Arg Thr Ser Ser Phe Ala Glu Gly Lys Lys
1               5                   10

<210> SEQ ID NO 37
<211> LENGTH: 4
<212> TYPE: PRT
<213> ORGANISM: artificial
<220> FEATURE:
<223> OTHER INFORMATION: Motif within sequence 2

<400> SEQUENCE: 37

Asn Pro Leu Tyr
1

<210> SEQ ID NO 38
<211> LENGTH: 10
<212> TYPE: PRT
<213> ORGANISM: Artificial
<220> FEATURE:
<223> OTHER INFORMATION: 10-mer peptide from B2 integrin cytoplasmic
      domains

<400> SEQUENCE: 38

Lys Glu Lys Leu Lys Asn Pro Leu Phe Lys
1               5                   10

<210> SEQ ID NO 39
<211> LENGTH: 10
<212> TYPE: PRT
<213> ORGANISM: Artificial
<220> FEATURE:
<223> OTHER INFORMATION: 10 mer peptide from B3 integrin cytoplasmic
      domain

<400> SEQUENCE: 39

Arg Ala Arg Ala Lys Asn Pro Leu Tyr Lys
1               5                   10

<210> SEQ ID NO 40
<211> LENGTH: 10
<212> TYPE: PRT
<213> ORGANISM: Artificial
<220> FEATURE:
<223> OTHER INFORMATION: 10 mer peptide from B5 integrin cytoplasmic
      domain

<400> SEQUENCE: 40

Arg Ser Arg Ala Arg Asn Pro Leu Tyr Arg
1               5                   10

<210> SEQ ID NO 41
<211> LENGTH: 10
<212> TYPE: PRT
<213> ORGANISM: Artificial
<220> FEATURE:
<223> OTHER INFORMATION: Variant of motif in sequence 37 with an alanine
      substitution for tyrosine
```

```
<400> SEQUENCE: 41

Arg Ser Lys Ala Lys Asn Pro Leu Ala Arg
1               5                   10

<210> SEQ ID NO 42
<211> LENGTH: 10
<212> TYPE: PRT
<213> ORGANISM: Artificial
<220> FEATURE:
<223> OTHER INFORMATION: Variant of motif in sequence 37 with a single
      alanine substitution for proline.

<400> SEQUENCE: 42

Arg Ser Lys Ala Lys Asn Ala Leu Tyr Arg
1               5                   10

<210> SEQ ID NO 43
<211> LENGTH: 26
<212> TYPE: PRT
<213> ORGANISM: Artificial
<220> FEATURE:
<223> OTHER INFORMATION: 10RVK peptide with penetratin coupled to its
      N-terminal

<400> SEQUENCE: 43

Arg Gln Ile Lys Ile Trp Phe Gln Asn Arg Arg Met Lys Trp Lys Lys
1               5                   10                  15

Arg Val Lys Val Lys Val Val Val Arg
            20                  25
```